US011845940B2

(12) United States Patent
Geiselman et al.

(10) Patent No.: US 11,845,940 B2
(45) Date of Patent: Dec. 19, 2023

(54) GENETICALLY MODIFIED FUNGAL CELLS AND METHODS USEFUL FOR PRODUCING PRESPATANE

(71) Applicants: THE REGENTS OF THE UNIVERSITY OF CALIFORNIA, Oakland, CA (US); NATIONAL TECHNOLOGY AND ENGINEERING SOLUTIONS OF SANDIA, LLC, Albuquerque, NM (US)

(72) Inventors: Gina Marie Geiselman, Alameda, CA (US); James Kirby, Berkeley, CA (US); Taek Soon Lee, Berkeley, CA (US); John M. Gladden, Alameda, CA (US); Blake A. Simmons, San Francisco, CA (US)

(73) Assignees: THE REGENTS OF THE UNIVERSITY OF CALIFORNIA, Oakland, CA (US); NATIONAL TECHNOLOGY & ENGINEERING SOLUTIONS OF SANDIA, LLC, Albuquerque, NM (US)

(*) Notice: Subject to any disclaimer, the term of this patent is extended or adjusted under 35 U.S.C. 154(b) by 10 days.

(21) Appl. No.: 17/187,697

(22) Filed: Feb. 26, 2021

(65) Prior Publication Data
US 2021/0269810 A1   Sep. 2, 2021

Related U.S. Application Data

(60) Provisional application No. 62/982,714, filed on Feb. 27, 2020.

(51) Int. Cl.
*C12N 15/81* (2006.01)
*C12N 9/88* (2006.01)
(Continued)

(52) U.S. Cl.
CPC .............. *C12N 15/815* (2013.01); *C10L 1/04* (2013.01); *C12N 1/16* (2013.01); *C12N 9/88* (2013.01);
(Continued)

(58) Field of Classification Search
CPC .......... C12N 15/815; C12N 1/16; C12N 9/88; C12Y 402/03037; C10L 1/04; C10L 2200/043; C10L 2270/04; C12P 5/007
See application file for complete search history.

(56) References Cited

U.S. PATENT DOCUMENTS 9,109,175 B2   8/2015  Lee et al.
10,323,198 B1  6/2019  Harvey

OTHER PUBLICATIONS

Liu et al. "Renewable production of high density jet fuel precursor sesquiterpenes from *Escherichia coli*", Oct. 20, 2018, Biotechnology for Biofuels, 1:285, p. 1-15. (Year: 2018).*
(Continued)

*Primary Examiner* — Gary B Nickol
*Assistant Examiner* — Amelia Nicole Dickens
(74) *Attorney, Agent, or Firm* — Robin C. Chiang; LAWRENCE BERKELEY NATIONAL LABORATORY

(57) ABSTRACT

The present invention provides for a genetically modified fungal host cell capable of producing prespatane and/or epi-isozizaene comprising prespatane synthase (PPS) and/or epi-isozizaene synthase (EIZS).

18 Claims, 13 Drawing Sheets

Specification includes a Sequence Listing.

(51) Int. Cl.
C12P 5/00 (2006.01)
C12N 1/16 (2006.01)
C10L 1/04 (2006.01)

(52) U.S. Cl.
CPC ....... *C12P 5/007* (2013.01); *C12Y 402/03037* (2013.01); *C10L 2200/043* (2013.01); *C10L 2270/04* (2013.01); *C10L 2290/26* (2013.01)

(56) References Cited

OTHER PUBLICATIONS

Lin et al. "Genome mining in Streptomyces coelicolor: molecular cloning and characterization of a new sesquiterpene synthase.", Apr. 19, 2006, J Am Chem Soc. vol. 128: p. 6022-6023. (Year: 2006).*
Supporting Information from Lin et al. "Genome mining in Streptomyces coelicolor: molecular cloning and characterization of a new sesquiterpene synthase.", Apr. 19, 2006, J Am Chem Soc. vol. 128: p. 6022-6023. (Year: 2006).*
Yaegashi et al., "Rhodosporidium toruloides: a new platform organism for conversion of lignocellulose into terpene biofuels and bioproducts." Oct. 23, 2017, Biotechnol Biofuels, 10:241, p. 1-13. (Year: 2017).*
Kersten et al., "A Red Algal Bourbonane Sesquiterpene Synthase Defined by Microgram-Scale NMR-Coupled Crystalline Sponge X-ray Diffraction Analysis." J Am Chem Soc. 2017;139:16838-44 (2017) (Year: 2017).*
Lee et al., Development of the Colle-Salvetti correlation-energy formula into a functional of the electron density. Phys Rev, B Condens Matter. 37:785-9 (1988).
Edwards, Reference jet fuels for combustion testing. In: 55th AIAA Aerospace Sciences Meeting. Reston, Virginia: American Institute of Aeronautics and Astronautics (2017).
Montgomery et al., "A complete basis set model chemistry. VII. Use of the minimum population localization method." J Chem Phys. 112: 6532 (2000).
Agrawal et al., "Molecular dynamics study of the melting of nitromethane." J Chem Phys. 119:9617-27 (2003).
Rodriguez A, Ersig N, Geiselman GM, Seibel K, Simmons BA, Magnuson JK, et al. Conversion of depolymerized sugars and aromatics from engineered feedstocks by two oleaginous red yeasts. Bioresour Technol. 286:121365 (2019).
Kim et al., "An asymmetric total synthesis of (+)-pentalenene." Tetrahedron. 69:7810-6 (2013).
Abramson et al., "Plant cell wall reconstruction toward improved lignocellulosic production and processability." Plant Sci. 178:61-72 (2010).
Ham et al., "Design, implementation and practice of JBEI-ICE: an open source biological part registry platform and tools." Nucleic Acids Res. 40:e141 (2012).
Abbott et al., "Overcoming recalcitrant transformation and gene manipulation in Pucciniomycotina yeasts." Appl Microbiol Biotechnol. 97:283-95 (2013).
Zhang et al., "Engineering Rhodosporidium toruloides for increased lipid production." Biotechnol Bioeng. 113:1056-66 (2016).
Li et al., "Comparison of dilute acid and ionic liquid pretreatment of switchgrass: Biomass recalcitrance, delignification and enzymatic saccharification." Bioresour Technol. 101:4900-6 (2010).
Gaswirth et al., "Assessment of undiscovered continuous oil and gas resources in the Wolfcamp Shale and Bone Spring Formation of the Delaware Basin, Permian Basin Province, New Mexico and Texas, 2018." USGS (2018).
Hunt et al., "The potential macroeconomic impact of the unconventional oil and gas boom in the united states." IMF Working Papers. 15:1 (2015).
Kaygusuz, "Energy for sustainable development: A case of developing countries." Renewable and Sustainable Energy Reviews. 16:1116-26 (2012).
Crespo et al., "Carbon Emission Trading Systems (ETS), Industry Business Dynamics, and the Aviation System: a survey on economic modeling and ETS implementation impacts assessment techniques" IATA. Economic Performance of the Airline Industry. 2019 Midyear. Montreal, Quebec, Canada: International Air Transport Association (2019).
Rye et al., "Sustainability of supply or the planet: a review of potential drop-in alternative aviation fuels." Energy Environ Sci. 3:17-27 (2010).
Wang et al., "Bio-jet fuel conversion technologies." Renewable and Sustainable Energy Reviews. 53:801-22 (2016).
Bond et al., "Production of renewable jet fuel range alkanes and commodity chemicals from integrated catalytic processing of biomass." Energy Environ Sci. 7:1500-23 (2014).
Harvey et al., "1-Hexene: a renewable C6 platform for full-performance jet and diesel fuels." Green Chem. 16:770-6 (2014).
Harvey et al., "The role of butanol in the development of sustainable fuel technologies." J Chem Technol Biotechnol. 86:2-9 (2011).
Harvey et al., "Synthesis of renewable jet and diesel fuels from 2-ethyl-1-hexene." Energy Environ Sci. 3:352 (2010).
Wright et al., "Highly Efficient Zirconium-Catalyzed Batch Conversion of 1-Butene: A New Route to Jet Fuels." Energy Fuels. 22:3299-302 (2008).
Renouard-Vallet et al., "Improving the environmental impact of civil aircraft by fuel cell technology: concepts and technological progress." Energy Environ Sci. 3:1458 (2010).
Savage, "Fuel options: The ideal biofuel" Nature. 474:S9-11 (2011).
Harrison et al., "Renewable high density fuels containing tricyclic sesquiterpanes and alkyl diamondoids." Sustainable Energy Fuels. 1:467-73 (2017).
Harvey et al., "High-Density Renewable Diesel and Jet Fuels Prepared from Multicyclic Sesquiterpanes and a 1-Hexene-Derived Synthetic Paraffinic Kerosene." Energy Fuels. 29:2431-6 (2015).
Harvey et al., "High-density biosynthetic fuels: the intersection of heterogeneous catalysis and metabolic engineering." Phys Chem Chem Phys. 16:9448-57 (2014).
Aaron et al., "Structure of epi-isozizaene synthase from Streptomyces coelicolor A3(2), a platform for new terpenoid cyclization templates." Biochemistry. 49:1787-97 (2010).
Lin et al., "Genome mining in Streptomyces coelicolor: molecular cloning and characterization of a new sesquiterpene synthase." J Am Chem Soc. 128:6022-3 (2006).
Takamatsu et al., "Characterization of a silent sesquiterpenoid biosynthetic pathway in Streptomyces avermitilis controlling epi-isozizaene albaflavenone biosynthesis and isolation of a new oxidized epi-isozizaene metabolite." Microb Biotechnol. 4:184-91 (2011).
Liu et al., "Renewable production of high density jet fuel precursor sesquiterpenes from *Escherichia coli*." Biotechnol Biofuels. 11:285 (2018).
Kersten et al., "A Red Algal Bourbonane Sesquiterpene Synthase Defined by Microgram-Scale NMR-Coupled Crystalline Sponge X-ray Diffraction Analysis." J Am Chem Soc. 2017;139:16838-44 (2017).
Baral et al., "Techno-economic analysis and life-cycle greenhouse gas mitigation cost of five routes to bio-jet fuel blendstocks." Energy Environ Sci. 12:807-24 (2019).
Ragauskas et al., "The path forward for biofuels and biomaterials." Science. 311:484-9 (2006).
Baral et al., "Approaches for more efficient biological conversion of lignocellulosic feedstocks to biofuels and bioproducts." ACS Sustain Chem Eng. 7:9062-79 (2019).
Wang et al., "Phylogenetic classification of yeasts and related taxa within Pucciniomycotina." Stud Mycol. 81:149-89 (2015).
Sundstrom et al., "Demonstrating a separation-free process coupling ionic liquid pretreatment, saccharification, and fermentation with Rhodosporidium toruloides to produce advanced biofuels." Green Chem. 20:2870-9 (2018).
Yaegashi et al., "Rhodosporidium toruloides: a new platform organism for conversion of lignocellulose into terpene biofuels and bioproducts." Biotechnol Biofuels. 10:241 (2017).
Zhuang et al., "Monoterpene production by the carotenogenic yeast Rhodosporidium toruloides." Microb Cell Fact. 18:54 (2019) 15 pages.

(56) References Cited

OTHER PUBLICATIONS

Xie et al., "A 5-Enolpyruvylshikimate 3-Phosphate Synthase Functions as a Transcriptional Repressor in Populus." Plant Cell. 30:1645-60 (2018).
Dou et al., "Can we use short rotation coppice poplar for sugar based biorefinery feedstock? Bioconversion of 2-year-old poplar grown as short rotation coppice." Biotechnol Biofuels. 10:144 (2017).
Poling BE, Prausnitz JM, O'Connell JP. The Properties of Gases and Liquids. 5th edition. New York: McGraw-Hill; 2001.
Ely et al., "Prediction of transport properties. 1. Viscosity of fluids and mixtures." Ind Eng Chem Fund. 20:323-32 (1981).
Pedersen et al., "Viscosity of crude oils." Chem Eng Sci. 39:1011-6 (1984).
Pedersen et al., "An improved corresponding states model for the prediction of oil and gas viscosities and thermal conductivities." Chem Eng Sci. 42:182-6 (1987).
Edwards, "Reference Jet Fuels for Combustion Testing." AIAA SciTech Forum, 2017.
Marrero et al., "Group-contribution based estimation of pure component properties." Fluid Phase Equilib. 183-184:183-208 (2001).
Agrawal et al., "Molecular dynamics simulations of hexahydro-1,3,5-trinitro-1,3,5-s-triazine (RDX) using a combined Sorescu-Rice-Thompson AMBER force field." J Phys Chem B. 110:26185-8 (2006).
Kosir et al., "Improvement in Jet Aircraft Operation with the Use of High-Performance Drop-in Fuels." In: AIAA Scitech 2019 Forum. Reston, Virginia: American Institute of Aeronautics and Astronautics (2019).
Coradetti et al. "Functional genomics of lipid metabolism in the oleaginous yeast Rhodosporidium toruloides." elife. 7: e32110 (2018).
Montet et al., "A study of the influence of the growth media on the fatty acid composition inCandida lipolytica diddens and lodder." Biotechnol Lett. 7:733-6 (1985).
Papanikolaou et al., "Kinetic profile of the cellular lipid composition in an oleaginous Yarrowia lipolytica capable of producing a cocoa-butter substitute from industrial fats." Antonie Van Leeuwenhoek. 80:215-24 (2001).
Papanikolaou et al., "Influence of glucose and saturated free-fatty acid mixtures on citric acid and lipid production by Yarrowia lipolytica." Curr Microbiol. 52:134-42 (2006).
Wehrs et al., "Sustainable bioproduction of the blue pigment indigoidine: Expanding the range of heterologous products in R. toruloides to include non-ribosomal peptides." Green Chem. (2019).
Bicho et al., "Induction of Xylose Reductase and Xylitol Dehydrogenase Activities in Pachysolen tannophilus and Pichia stipitis on Mixed Sugars." Appl Environ Microbiol. 54:50-4 (1988).
Lee "Reversible inactivation of d-xylose utilization by d-glucose in the pentose-fermenting yeast Pachysolen tannophilus." FEMS Microbiol Lett. 92:1-4 (1992).
Wedlock et al., "Glucose-negative Mutants of Pachysolen tannophilus." MICROBIOLOGY. 135:2019-26 (1989).
Dashtban et al., "Deletion of hxk1 gene results in derepression of xylose utilization in Scheffersomyces stipitis." J Ind Microbiol Biotechnol. 42:889-96 (2015).
Stein et al., "Estimation of normal boiling points from group contributions." J Chem Inf Model. 34:581-7 (1994).
Joback et al., Estimation of pure-component properties from group-contributions. Chem Eng Commun. 57:233-43 (1987).
Becke, "Density-functional thermochemistry. I. The effect of the exchange-only gradient correction" J. Chem. Phys. 96, 2155-2160 (1992).
Rodriguez et al., "Conversion of depolymerized sugars and aromatics from engineered feedstocks by two oleaginous red yeasts." Bioresour Technol. 286:121365 (2019).
Geiselman et al., "Conversion of poplar biomass into high-energy density tricyclic sesquiterpene jet fuel blendstocks", Microbial Cell Factories, 19: 208 (2020), 16 pages.

* cited by examiner

| Medium | Supplement | Glucose utilization (%) | Xylose utilization (%) | Glucose yield (mg/g) | Xylose yield (mg/g) |
|---|---|---|---|---|---|
| Hydrolysate | (NH$_4$)$_2$SO$_4$ 5 | 99.4 ± 0.2 | 86.1 ± 0.8 | 6.4 | 21.4 |
| | (NH$_4$)$_2$SO$_4$ 10 | 98.0 ± 0.9 | 88.9 ± 0.9 | 6.7 | 22.5 |
| | (NH$_4$)$_2$SO$_4$ 5 / Synthetic Defined / gluc 40 | 99.8 ± 0.0 | 97.6 ± 0.1 | 9.3 | 64.8 |
| | Yeast extract 10 | 98.1 ± 1.0 | 77 ± 0.8 | 3.3 | 11.2 |
| Control | - | 100.0 ± 0.0 | - | 2.6 | - |

| Hydrolysate | Glucose yield (mg/g) | Xylose yield (mg/g) |
|---|---|---|
| Filtered | 16.6 | 46.9 |
| Mock | 2.8 | 8.8 |
| Unfiltered | 5.3 | 14.5 |

| Strain | Condition | Glucose utilization (%) | Xylose utilization (%) |
|---|---|---|---|
| EIZS2 | Hydrolysate | 99.24 ± 0.05 | 28.84 ± 6.33 |
|  | Mock | 99.86 ± 0.25 | 99 ± 0.95 |
| PPS5 | Hydrolysate | 97.73 ± 0.04 | 15.93 ± 0.96 |
|  | Mock | 100 ± 0 | 96.85 ± 0.07 |

GENETICALLY MODIFIED FUNGAL CELLS AND METHODS USEFUL FOR PRODUCING PRESPATANE

CROSS REFERENCE TO RELATED APPLICATIONS

This application claims priority to U.S. Provisional Patent Application Ser. No. 62/982,714, filed Feb. 27, 2020, which is incorporated by reference in its entirety.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of the production of tricyclic sesquiterpenes, which are aviation and missile fuel precursors.

REFERENCE TO A "SEQUENCE LISTING" SUBMITTED AS ASCII TEXT FILES VIA EFS-WEB

The Sequence Listing written in file 2019-014-02_Sequence_Listing_ST25.txt created on Feb. 26, 2021, 7,119 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

New oil discoveries (Gaswirth et al. 2018) and improved technologies to extract non-traditional oil resources (Hunt et al. 2015) can temporarily lower the cost of oil but the demand from exponential global population growth makes this trend unsustainable (Kaygusuz 2012). More importantly, in the last six years there has been an estimated 31% increase in global petroleum-derived jet fuel consumption, projected with almost 1 trillion kg of CO2 emissions in 2019 (IATA 2019). With jet fuel accounting for 9% of the total greenhouse gas emissions associated with the transportation sector (EIA 2016), the development of renewable alternatives to jet and diesel fuel continues to be an important priority (Wang and Tao 2016; Bond et al. 2014; Harvey and Meylemans 2014; Harvey and Meylemans 2011; Harvey and Quintana 2010; Wright et al. 2008). In an effort to decarbonize sectors, road transportation is shifting towards electrification, while aviation remains dependent on non-renewable liquid fuels, despite an increase in airline passenger traffic of over 5% per year since 2000 (Renouard-Vallet et al. 2010; Savage 2011).

Due to their high cetane numbers and energy densities, a number of tricyclic sesquiterpenes have been identified as potential components of next-generation renewable jet fuels (Harvey et al. 2015; Harvey et al. 2014). A fuel blend based on hydrogenated cedarwood oil (composed primarily of the tricyclic sesquiterpenes thujopsene, α-cedrene, and β-cedrene) was found to have a volumetric net heat of combustion (NHOC) more than 12% higher than conventional jet fuel Morrison and Harvey 2017). Two tricyclic sesquiterpenes, epi-isozizaene and prespatane, are investigated here for suitability as candidate renewable jet fuel blend. Epi-isozizaene (FIG. 1A), is produced by several Streptomyces species and initially sparked interest as a candidate jet fuel on account of having a specific energy similar to that of jet fuel A-1 (Aaron et al. 2010; Kim et al. 2013; Lin et al. 2006; Takamatsu et al. 2011; Liu et al. 2018), while prespatane (FIG. 1B) is a little-known sesquiterpene produced by the red macroalga, Laurencia pacifica (Kersten et al. 2017). A simulation entailing a consolidated bioreactor utilizing a sorghum feedstock and an integrated ionic liquid (IL) based biomass deconstruction process followed by high-gravity fermentation into saturated terpene jet fuel candidates, such as epi-isozizaene, could produce a candidate Jet A replacement fuel with a minimum selling price of $0.73-$0.91 per liter ($2.75-$3.45 per gallon) (Baral et al. 2019).

SUMMARY OF THE INVENTION

The present invention provides for a genetically modified fungal host cell capable of producing prespatane and/or epi-isozizaene comprising prespatane synthase (PPS) and/or epi-isozizaene synthase (EIZS).

In some embodiments, the genetically modified fungal host cell is a yeast host cell. In some embodiments, the yeast host cell is a basidiomycete. In some embodiments, the yeast host cell is an oleaginous yeast. In some embodiments, the oleaginous yeast is a Rhodosporidium species. In some embodiments, the Rhodosporidium species is Rhodosporidium toruloides. In some embodiments, the Rhodosporidium toruloides is strain IFO 0880.

In some embodiments, the PPS comprises an amino acid sequence having at least 70% identity with SEQ ID NO:1. In some embodiments, the EIZS comprises an amino acid sequence having at least 70% identity with SEQ ID NO:2.

In some embodiments, one or more, or all of the enzymes of the mevalonate (MVA) pathway is native to the genetically modified fungal host cell. In some embodiments, one or more, or all of the enzymes of the mevalonate (MVA) pathway is heterologous to the genetically modified fungal host cell.

In some embodiments, the genetically modified fungal host cell further comprises one or enzymes of the mevalonate (MVA) pathway, wherein the MVA pathway is heterologous to the genetically modified host cell. In some embodiments, the genetically modified host cell further comprises acetoacetyl-CoA thiolase (AtoB), HMG-CoA synthase (HMGS), HMG-CoA reductase (HMGR), mevalonate kinase (MK), phosphomevalonate kinase (PMK), mevalonate diphosphate decarboxylase (PMD), isopentenyl diphosphate (IPP) isomerase (Idi), and farnesyl diphosphate (FPP) synthase (IspA), which are Isa heterologous to the genetically modified host cell.

The present invention provides for a method for producing prespatane and/or epi-isozizaene comprising: (a) providing a genetically modified fungal host cell of claim 1, (b) culturing or growing the genetically modified host cell in a suitable culture or medium such that prespatane and/or epi-isozizaene is produced, (c) optionally extracting or separating the prespatane and/or epi-isozizaene from the fungal host cells, and/or culture or medium, (d) optionally hydrogenating the prespatane and/or epi-isozizaene extracted or separated from the fungal host cells, and/or culture or medium, and (e) optionally introducing a fuel additive to the extracted or separated prespatane and/or epi-isozizaene.

The present invention provides for a fuel composition comprising: (a) a prespatane or a saturated product of a prespatane; and (b) a fuel additive.

In some embodiments, the providing step (a) comprises introducing a nucleic acid encoding the prespatane synthase (PPS) and/or epi-isozizaene synthase (EIZS) operatively linked to a promoter capable of expressing the prespatane synthase (PPS) and/or epi-isozizaene synthase (EIZS) in the fungal host cell into the host cell. In some embodiments, the culturing or growing step (b) comprises the fungal host cell growing by respiratory cell growth. In some embodiments, the culturing or growing step (b) takes place in a batch process or a fed-batch process, such as a high-gravity fed-batch process.

In some embodiments, the culture comprises a biomass, such as a lignocellulosic biomass, or hydrolysate thereof. In some embodiments, the biomass is obtained from softwood feedstock (such as poplar), hardwood feedstock, grass feedstock, and/or agricultural feedstock, or mixture thereof.

In some embodiments, the culture or medium comprises a rich medium, such as LB (Lysogeny-Broth) or comprising one or more ingredients of LB, such as tryptone and/or yeast extract. In some embodiments, the culture or medium comprises hydrolysates derived or obtained from a biomass, such as a lignocellulosic biomass. In some embodiments, the culture or medium comprises one or more carbon sources, such as a sugar, such as glucose or galactose, or glycerol, or a mixture thereof. In some embodiments, the carbon source is fermentable. In some embodiments, the carbon source is non-fermentable. In some embodiments, the culture or medium comprises urea as a nitrogen source. In some embodiments, the culture or medium comprises an ionic liquid (IL).

In some embodiments, the method results in the genetically modified fungal host cell producing equal to or more than about 10 mg/L, 20 mg/L, 30 mg/L, 40 mg/L, 50 mg/L, 60 mg/L, 70 mg/L, 80 mg/L, 90 mg/L, 100 mg/L, 150 mg/L, 200 mg/L, 250 mg/L, 300 mg/L, 350 mg/L, or 400 mg/L of prespatane and/or epi-isozizaene. In some embodiments, the method results in the genetically modified fungal host cell producing equal to or more than about 1 g/L of prespatane and/or epi-isozizaene.

The present invention provides for a method for constructing a genetically modified fungal host cell of the present invention, comprising (a) introducing a nucleic acid encoding the prespatane synthase (PPS) and/or epi-isozizaene synthase (EIZS) operatively linked to a promoter capable of expressing the prespatane synthase (PPS) and/or epi-isozizaene synthase (EIZS) in the host cell into the host cell. In some embodiments, the prespatane synthase (PPS) and/or epi-isozizaene synthase (EIZS) is heterologous to the host cell.

In some embodiments, the invention comprises the use of a heterologous codon-optimized version of the nucleic acid encoding the prespatane synthase (PPS) and/or epi-isozizaene synthase (EIZS), which are optimized to the fungal host cell.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1A:
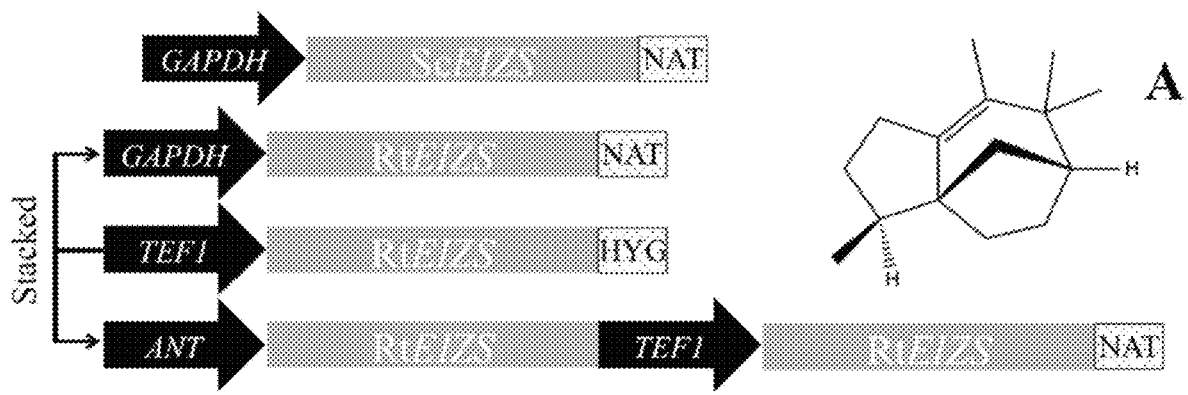
FIG. 1A. Constructs of relevant plasmids as well as their product chemical structures: epi-isozizaene. Arrows labeled "stacked" represent TEF1-HYG constructs used to transform onto highest perspective sesquiterpene producing strains with NAT resistance to increase gene copy number. Rt represents R. toruloides codon optimized genes while Sc and Lp represent native genes from S. coelicolor and L. pacifica.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

The term "about" refers to a value including 10% more than the stated value and 10% less than the stated value.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The terms "host cell" is used herein to refer to a living biological cell that can be transformed via insertion of an expression vector.

The term "heterologous" as used herein refers to a material, or nucleotide or amino acid sequence, that is found in or is linked to another material, or nucleotide or amino acid sequence, wherein the materials, or nucleotide or amino acid sequences, are foreign to each other (i.e., not found or linked together in nature).

The terms "expression vector" or "vector" refer to a compound and/or composition that transduces, transforms, or infects a host cell, thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular species, but also encompasses a promoter from a corresponding gene in other species.

A polynucleotide is "heterologous" to a host cell or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

The term "operatively linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The present invention provides a production of a novel jet fuel molecule, the tricyclic sesquiterpene prespatane, in the red yeast *Rhodosporidium toruloides* from a renewable carbon source, such as lignocellulosic biomass. In some embodiments, prespatane synthase from *Laurencia pacifica* is introduced into *R. toruloides* and tested for production from simple to complex carbon sources and in lignocellulosic biomass. In some embodiments, the prespatane is produced using a one-pot pretreatment saccharification and fermentation process.

In some embodiments, codon optimized prespatane synthase from *Laurencia pacifica* is randomly integrated into the *Rhodosporidium toruloides* IFO 0880 genome. High titer of the novel jet fuel, prespatane is achieved. The use of a lignocellulosic biomass increases the titer.

In some embodiments, the prespatane sesquiterpene synthase (PPS), or a homologous enzyme thereof, has an amino acid sequence having at least 70%, 80%, 90%, 95%, or 99% identity to the amino acid sequence of *Laurencia pacifica* prespatane sesquiterpene synthase which is as follows:

```
                                            (SEQ ID NO: 1)
         10         20         30         40
MSLANNIAPT HSMRSDSVEV GENKLRFTSF TSFGDEFINE 50         60         70         80
HEAPAFIESV AWFQSLNAIA TPQHLKIVKN ATFERLVSRT 90        100        110        120
FPFADLAGAR IATDLMILTF LIDDLSDVVE ATDDTAMHAM 130        140        150        160
SAVEGQVTHV LRGGTPRPGE HPLAVAMRSI VDRAMLTYNP 170        180        190        200
DWIDLMRKEF ITYLEMNRLE RINRLEGPGL SWTMFENTRY 210        220        230        240
YSSCVLPFLY LSAGMGCTGC PSTVLSVPFV KIMTDLTVNH 250        260        270        280
VAWVNDIVGA NKERKEAVNN NIVFVIANDR GLTMAGAVKD 290        300        310        320
AVKRTNQECE VFLNLEHRLH AGGAVVDGDD LFNYIEVLKY 330        340
WMRGSLDWHF ESKRYKVKAS K
```

In some embodiments, the epi-isozizaene synthase (EIZS), or a homologous enzyme thereof, has an amino acid sequence having at least 70%, 80%, 90%, 95%, or 99% identity to the amino acid sequence of *Streptomyces coelicolor* epi-isozizaene synthase which is as follows:

```
                                            (SEQ ID NO: 2)
         10         20         30         40
MHAFPHGTTA TPTAIAVPPS LRLPVIEAAF PRQLHPYWPK 50         60         70         80
LQETTRTWLL EKRLMPADKV EEYADGLCYT DLMAGYYLGA 90        100        110        120
PDEVLQAIAD YSAWFFVWDD RHDRDIVHGR AGAWRRLRGL 130        140        150        160
LHTALDSPGD HLHHEDTLVA GFADSVRRLY AFLPATWNAR 170        180        190        200
FARHFHTVIE AYDREFHNRT RGIVPGVEEY LELRRLTFAH 210        220        230        240
WIWTDLLEPS SGCELPDAVR KHPAYRRAAL LSQEFAAWYN
        250        260        270        280
DLCSLPKEIA GDEVHNLGIS LITHHSLTLE EAIGEVRRRV 290        300        310        320
EECITEFLAV ERDALRFADE LADGTVRGKE LSGAVRANVG 330        340        350        360
NMRNWFSSVY WFHHESGRYM VDSWDDRSTP PYVNNEAAGE K
```

In some embodiments, the PPS and/or EIZS comprise the amino acid sequence Asp-Asp-Xaa-Xaa-Asp (DDXXD) (SEQ ID NO:3) or Asp-Asp-Xaa-Xaa-Glu (DDXXE) (SEQ ID NO:4) motif, which is important for the catalytic activity of PPS and EIZS, presumably through binding to $Mg^{2+}$.

In some embodiments, the nucleic acid encoding PPS or EIZS is codon optimized for that fungal cell. In some embodiments, when the host cell is a *Rhodosporidium* cell, such as a *Rhodosporidium toruloides*, the nucleic acid encoding PPS or EIZS has an increase of GC-content of at least about 1%, 2%, 3%, 4%, 5%, 6%, 7%, 8%, 9%, 10%, 11%, 12%, 13%, or 14%, and/or there are fewer, or no, ATA, CTA, TTA, AGA, and/or GTA codons, when compared to the codons used in the native genes encoding *Laurencia pacifica* prespatane sesquiterpene synthase or *Streptomyces coelicolor* epi-isozizaene synthase.

In some embodiments, the fungal host cell comprises a nucleic acid encoding the one or more enzymes operatively linked to a promoter capable of expressing the one or more enzymes in the fungal host cell. In some embodiments, the encoding of the one or more enzymes to the nucleic acid is codon optimized to the fungal host cell. In some embodiments, the nucleic acid is vector or replicon that can stably reside in the fungal host cell. In some embodiments, the nucleic acid is stably integrated into one or more chromosomes of the fungal host cell.

In some embodiments, the providing step (a) comprises introducing a nucleic acid encoding the one or more enzymes operatively linked to a promoter capable of expressing the one or more enzymes in the host cell into the host cell.

In some embodiments, the culturing or growing step (b) comprises the fungal host cell growing by respiratory cell growth. In some embodiments, the culturing or growing step (b) takes place in a batch process or a fed-batch process, such as a high-gravity fed-batch process. In some embodiments, the culture or medium comprises hydrolysates derived or obtained from a biomass, such as a lignocellulosic biomass. In some embodiments, the culture or medium comprises one or more carbon sources, such as a sugar, such as glucose or galactose, or glycerol, or a mixture thereof. In some embodiments, the carbon source is fermentable. In some embodiments, the carbon source is non-fermentable.

The present invention provides for a method for constructing a genetically modified fungal host cell of the present invention, comprising (a) introducing a nucleic acid encoding the one or more enzymes operatively linked to a promoter capable of expressing the one or more enzymes in the host cell into the host cell.

One can modify the expression of a gene encoding any of the enzymes taught herein by a variety of methods in accordance with the methods of the invention. Those skilled in the art would recognize that increasing gene copy number, ribosome binding site strength, promoter strength, and various transcriptional regulators can be employed to alter an enzyme expression level.

The biomass can be obtained from one or more feedstock, such as softwood feedstock, hardwood feedstock, grass feedstock, and/or agricultural feedstock, or a mixture thereof.

Softwood feedstocks include, but are not limited to, *Araucaria* (e.g. *A. cunninghamii, A. angustifolia, A. araucana*); softwood Cedar (e.g. *Juniperus virginiana, Thuja plicata, Thuja occidentalis, Chamaecyparis thyoides Callitropsis nootkatensis*); Cypress (e.g. *Chamaecyparis, Cupressus Taxodium, Cupressus arizonica, Taxodium distichum, Chamaecyparis obtusa, Chamaecyparis lawsoniana, Cupressus sempervirens*); Rocky Mountain Douglas fir; European Yew; Fir (e.g. *Abies balsamea, Abies alba, Abies procera, Abies amabilis*); Hemlock (e.g. *Tsuga canadensis, Tsuga mertensiana, Tsuga heterophylla*); Kauri; Kaya; Larch (e.g. *Larix decidua, Larix kaempferi, Larix laricina, Larix occidentalis*); Pine (e.g. *Pinus nigra, Pinus banksiana, Pinus contorta, Pinus radiata, Pinus ponderosa, Pinus resinosa, Pinus sylvestris, Pinus strobus, Pinus monticola, Pinus lambertiana, Pinus taeda, Pinus palustris, Pinus rigida, Pinus echinata*); Redwood; Rimu; Spruce (e.g. *Picea abies, Picea mariana, Picea rubens, Picea sitchensis, Picea glauca*); Sugi; and combinations/hybrids thereof.

For example, softwood feedstocks which may be used herein include cedar; fir; pine; spruce; and combinations thereof. The softwood feedstocks for the present invention may be selected from loblolly pine (*Pinus taeda*), radiata pine, jack pine, spruce (e.g., white, interior, black), Douglas fir, *Pinus silvestris, Picea abies*, and combinations/hybrids thereof. The softwood feedstocks for the present invention may be selected from pine (e.g. *Pinus radiata, Pinus taeda*); spruce; and combinations/hybrids thereof.

Hardwood feedstocks include, but are not limited to, *Acacia; Afzelia; Synsepalum duloificum; Albizia*; Alder (e.g. *Alnus glutinosa, Alnus rubra*); Applewood; Arbutus; Ash (e.g. *F. nigra, F. quadrangulata, F. excelsior, F. pennsylvanica lanceolata, F. latifolia, F. profunda, F. americana*); Aspen (e.g. *P. grandidentata, P. tremula, P. tremuloides*); Australian Red Cedar (*Toona ciliata*); Ayna (*Distemonanthus benthamianus*); Balsa (*Ochroma pyramidale*); Basswood (e.g. *T. americana, T. heterophylla*); Beech (e.g. *F. sylvatica, F. grandifolia*); Birch; (e.g. *Betula populifolia, B. nigra, B. papyrifera, B. lenta, B. alleghaniensis/B. lutea, B. pendula, B. pubescens*); Blackbean; Blackwood; Bocote; Boxelder; Boxwood; Brazilwood; Bubing a; Buckeye (e.g. *Aesculus hippocastanum, Aesculus glabra, Aesculus flava/ Aesculus octandra*); Butternut; *Catalpa*; Chemy (e.g. *Prunus serotina, Prunus pennsylvanica, Prunus avium*); Crabwood; Chestnut; Coachwood; Cocobolo; Corkwood; Cottonwood (e.g. *Populus balsamifera, Populus deltoides, Populus sargentii, Populus heterophylla*); Cucumbertree; Dogwood (e.g. *Cornus florida, Cornus nuttallii*); Ebony (e.g. *Diospyros kurzii, Diospyros melanida, Diospyros crassiflora*); Elm (e.g. *Ulmus americana, Ulmus procera, Ulmus thomasii, Ulmus rubra, Ulmus glabra*); Eucalyptus; Greenheart; Grenadilla; Gum (e.g. *Nyssa sylvatica, Eucalyptus globulus, Liquidambar styraciflua, Nyssa aquatica*); Hickory (e.g. *Carya alba, Carya glabra, Carya ovata, Carya laciniosa*); Hornbeam; Hophornbeam; Ipe; Iroko; Ironwood (e.g. Bangkirai, *Carpinus caroliniana, Casuarina equisetifolia, Choricbangarpia subargentea, Copaifera* spp., *Eusideroxylon zwageri, Guajacum officinale, Guajacum sanctum, Hopea odorata*, Ipe, Krugiodendronferreum, *Lyonothamnus lyonii* (*L. floribundus*), *Mesua ferrea, Olea* spp., *Olneya tesota, Ostrya virginiana, Parrotia persica, Tabebuia serratifolia*); *Jacaranda*; Jotoba; Lacewood; Laurel; Limba; *Lignum vitae*; Locust (e.g. *Robinia pseudacacia, Gleditsia triacanthos*); Mahogany; Maple (e.g. *Acer saccharum, Acer nigrum, Acer negundo, Acer rubrum, Acer saccharinum, Acer pseudoplatanus*); Meranti; Mpingo; Oak (e.g. *Quercus macrocarpa, Quercus alba, Quercus stellata, Quercus bicolor, Quercus virginiana, Quercus michauxii, Quercus prinus, Quercus muhlenbergii, Quercus chrysolepis, Quercus lyrata, Quercus robur, Quercus petraea, Quercus rubra, Quercus velutina, Quercus laurifolia, Quercus falcata, Quercus nigra, Quercus phellos, Quercus texana*); Obeche; Okoumé; Oregon Myrtle; California Bay Laurel; Pear; Poplar (e.g. *P. balsamifera, P. nigra*, Hybrid Poplar (*Populus×canadensis*)); Ramin; Red cedar; Rosewood; Sal; Sandalwood; *Sassafras*; Satinwood; Silky Oak; Silver Wattle; Snakewood; Sourwood; Spanish cedar; American sycamore; Teak; Walnut (e.g. *Juglans nigra, Juglans regia*); Willow (e.g. *Salix nigra, Salix alba*); Yellow poplar (*Liriodendron tulipifera*); Bamboo; Palmwood; and combinations/hybrids thereof.

For example, hardwood feedstocks for the present invention may be selected from *Acacia*, Aspen, Beech, *Eucalyptus*, Maple, Birch, Gum, Oak, Poplar, and combinations/ hybrids thereof. The hardwood feedstocks for the present invention may be selected from *Populus* spp. (e.g. *Populus tremuloides*), *Eucalyptus* spp. (e.g. *Eucalyptus globulus*), *Acacia* spp. (e.g. *Acacia dealbata*), and combinations thereof.

Grass feedstocks include, but are not limited to, $C_4$ or $C_3$ grasses, e.g. Switchgrass, Indiangrass, Big Bluestem, Little Bluestem, Canada Wildrye, Virginia Wildrye, and Goldenrod wildflowers, etc, amongst other species known in the art.

Agricultural feedstocks include, but are not limited to, agricultural byproducts such as husks, stovers, foliage, and the like. Such agricultural byproducts can be derived from crops for human consumption, animal consumption, or other non-consumption purposes. Such crops can be corps such as corn, wheat, rice, soybeans, hay, potatoes, cotton, or sugarcane.

The feedstock can arise from the harvesting of crops from the following practices: intercropping, mixed intercropping, row cropping, relay cropping, and the like.

In some embodiments, the fuel composition further comprises pentalenene, α-isocomene, α-zingiberene, β-sesquiphellandrene, α-bisabolene, β-bisabolene, γ-bisabolene, curcumene, gossonorol, or any monocyclic sesquiterpene taught in U.S. Pat. No. 9,109,175 (herein incorporated by reference), or a mixture thereof.

In one embodiment, the fuel additive that is mixed with the hydrogenation product of the prespatane and/or epi-isozizaene is a chemical compound or component added to the fuel composition to alter the property of the fuel, e.g., to improve engine performance, fuel handling, fuel stability, or for contaminant control, etc. The nature and amount of the one or more additives depends on the desired use of the final fuel composition. Some nonlimiting examples of conventional fuel additives include antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, emulsifiers, dyes, markers, static dissipaters, biocides, and combinations thereof.

In some embodiments, the fuel composition of the present invention may further comprise a conventional fuel component derived from petroleum, coal, wood, or any other hydrocarbon source. Nonlimiting examples of conventional fuel components include, but are not limited to, diesel fuels, jet fuels, kerosene, gasoline, and Fischer-Tropsch derived fuels. In some embodiments, the conventional fuel component is derived from petroleum or coal. In certain embodiments, the fuel component is or comprises a diesel fuel, a jet fuel, kerosene, gasoline, or a combination thereof. In other embodiments, the fuel component is or comprises a distillate diesel fuel.

In certain embodiments, the fuel composition of the present invention is intended for use in diesel engines. In other embodiments, the fuel composition of the present invention is intended for use in jet engines and/or missile propulsion systems. As such, the fuel compositions disclosed herein can be used as a fuel for internal combustion engines such as gasoline engines, diesel engines, jet engines, and/or missile propulsion systems.

In yet another aspect, the present invention provides a vehicle comprising an internal combustion engine, a fuel tank connected to the internal combustion engine, and a fuel composition in the fuel tank, wherein the fuel composition is the fuel composition as disclosed herein (e.g., hydrogenated tricyclic sesquiterpene), wherein the fuel combustion is used to power the internal combustion engine. In one embodiment, the internal combustion engine is a diesel engine. In another embodiment, the internal combustion engine is a jet engine or missile propulsion system.

In a further aspect, the present invention provides a method of powering an engine comprising the step of combusting a fuel composition of the present invention in the engine. In one embodiment, the engine is a diesel engine. In another embodiment, the engine is a jet engine or a missile propulsion system.

Other objects, features, and advantages of the present invention will be apparent to one of skill in the art from the following detailed description and figures.

REFERENCES CITED HEREIN

1. Gaswirth S B, French K L, Pitman J K, Marra K R, Mercier T J, Leathers-Miller H M, et al. Assessment of undiscovered continuous oil and gas resources in the Wolfcamp Shale and Bone Spring Formation of the Delaware Basin, Permian Basin Province, N. Mex. and Texas, 2018. USGS. 2018.
2. Hunt B, BHunt@imf.org, Muir D, DMuir@imf.org, Sommer M, MSommer@imf.org. The potential macroeconomic impact of the unconventional oil and gas boom in the united states. IMF Working Papers. 2015; 15:1. doi: 10.5089/9781484353189.001.
3. Kaygusuz K. Energy for sustainable development: A case of developing countries. Renewable and Sustainable Energy Reviews. 2012; 16:1116-26. doi:10.1016/j.rser.2011.11.013.
4. IATA. Economic Performance of the Airline Industry. 2019 Mid-year. Montreal, Quebec, Canada: International Air Transport Association; 2019.
5. E I A. Petroleum & Other Liquids. Washington, D.C.: U.S. Energy Information Administration; 2016.
6. Rye L, Blakey S, Wilson C W. Sustainability of supply or the planet: a review of potential drop-in alternative aviation fuels. Energy Environ Sci. 2010; 3:17-27. doi: 10.1039/B918197K.
7. Wang W-C, Tao L. Bio-jet fuel conversion technologies. Renewable and Sustainable Energy Reviews. 2016; 53:801-22. doi:10.1016/j.rser.2015.09.016.
8. Bond J Q, Upadhye A A, Olcay H, Tompsett G A, Jae J, Xing R, et al. Production of renewable jet fuel range alkanes and commodity chemicals from integrated catalytic processing of biomass. Energy Environ Sci. 2014; 7:1500-23. doi:10.1039/C3EE43846E.
9. Harvey B G, Meylemans H A. 1-Hexene: a renewable C6 platform for full-performance jet and diesel fuels. Green Chem. 2014; 16:770-6. doi:10.1039/C3GC41554F.
10. Harvey B G, Meylemans H A. The role of butanol in the development of sustainable fuel technologies. J Chem Technol Biotechnol. 2011; 86:2-9. doi:10.1002/jctb.2540.
11. Harvey B G, Quintana R L. Synthesis of renewable jet and diesel fuels from 2-ethyl-1-hexene. Energy Environ Sci. 2010; 3:352. doi:10.1039/b924004g.
12. Wright M E, Harvey B G, Quintana R L. Highly Efficient Zirconium-Catalyzed Batch Conversion of 1-Butene: A New Route to Jet Fuels. Energy Fuels. 2008; 22:3299-302. doi:10.1021/ef800380b.
13. Renouard-Vallet G, Saballus M, Schmithals G, Schirmer J, Kallo J, Friedrich K A. Improving the environmental impact of civil aircraft by fuel cell technology: concepts and technological progress. Energy Environ Sci. 2010; 3:1458. doi:10.1039/b925930a.
14. Savage N. Fuel options: The ideal biofuel. Nature. 2011; 474:59-11. doi:10.1038/474S09a.
15. Harrison K W, Harvey B G. Renewable high density fuels containing tricyclic sesquiterpanes and alkyl diamondoids. Sustainable Energy Fuels. 2017; 1:467-73. doi:10.1039/C6SE00108D.
16. Harvey B G, Merriman W W, Koontz T A. High-Density Renewable Diesel and Jet Fuels Prepared from Multicyclic Sesquiterpanes and a 1-Hexene-Derived Synthetic Paraffinic Kerosene. Energy Fuels. 2015; 29:2431-6. doi: 10.1021/ef5027746.
17. Harvey B G, Meylemans H A, Gough R V, Quintana R L, Garrison M D, Bruno T J. High-density biosynthetic fuels: the intersection of heterogeneous catalysis and metabolic engineering. Phys Chem Chem Phys. 2014; 16:9448-57. doi:10.1039/c3cp55349c.
18. Aaron J A, Lin X, Cane D E, Christianson D W. Structure of epi-isozizaene synthase from *Streptomyces coelicolor* A3(2), a platform for new terpenoid cyclization templates. Biochemistry. 2010; 49:1787-97. doi:10.1021/bi902088z.
19. Kim Y-J, Yoon Y, Lee H-Y. An asymmetric total synthesis of (+)-pentalenene. Tetrahedron. 2013; 69:7810-6. doi:10.1016/j.tet.2013.05.095.
20. Lin X, Hopson R, Cane D E. Genome mining in *Streptomyces coelicolor*: molecular cloning and characterization of a new sesquiterpene synthase. J Am Chem Soc. 2006; 128:6022-3. doi:10.1021/ja061292s.
21. Takamatsu S, Lin X, Nara A, Komatsu M, Cane D E, Ikeda H. Characterization of a silent sesquiterpenoid biosynthetic pathway in *Streptomyces avermitilis* controlling epi-isozizaene albaflavenone biosynthesis and isolation of a new oxidized epi-isozizaene metabolite. Microb Biotechnol. 2011; 4:184-91. doi:10.1111/j.1751-7915.2010.00209.x.

22. Liu C-L, Tian T, Alonso-Gutierrez J, Garabedian B, Wang S, Baidoo E E K, et al. Renewable production of high density jet fuel precursor sesquiterpenes from *Escherichia coli*. Biotechnol Biofuels. 2018; 11:285. doi:10.1186/s13068-018-1272-z.
23. Kersten R D, Lee S, Fujita D, Pluskal T, Kram S, Smith J E, et al. A Red Algal Bourbonane Sesquiterpene Synthase Defined by Microgram-Scale NMR-Coupled Crystalline Sponge X-ray Diffraction Analysis. J Am Chem Soc. 2017; 139:16838-44. doi:10.1021/jacs.7b09452.
24. Baral N R, Kavvada O, Mendez-Perez D, Mukhopadhyay A, Lee T S, Simmons B A, et al. Techno-economic analysis and life-cycle greenhouse gas mitigation cost of five routes to bio-jet fuel blendstocks. Energy Environ Sci. 2019; 12:807-24. doi:10.1039/C8EE03266A.
25. Ragauskas A J, Williams C K, Davison B H, Britovsek G, Cairney J, Eckert C A, et al. The path forward for biofuels and biomaterials. Science. 2006; 311:484-9. doi:10.1126/science.1114736.
26. Baral N R, Sundstrom E R, Das L, Gladden J M, Eudes A, Mortimer J, et al. Approaches for more efficient biological conversion of lignocellulosic feedstocks to biofuels and bioproducts. ACS Sustain Chem Eng. 2019; 7:9062-79. doi:10.1021/acssuschemeng.9b01229.
27. Wang Q M, Yurkov A M, Göker M, Lumbsch H T, Leavitt S D, Groenewald M, et al. Phylogenetic classification of yeasts and related taxa within Pucciniomycotina. Stud Mycol. 2015; 81:149-89. doi:10.1016/j.simyco.2015.12.002.
28. Sundstrom E, Yaegashi J, Yan J, Masson F, Papa G, Rodriguez A, et al. Demonstrating a separation-free process coupling ionic liquid pretreatment, saccharification, and fermentation with *Rhodosporidium toruloides* to produce advanced biofuels. Green Chem. 2018; 20:2870-9. doi:10.1039/C8GC00518D.
29. Rodriguez A, Ersig N, Geiselman G M, Seibel K, Simmons B A, Magnuson J K, et al. Conversion of depolymerized sugars and aromatics from engineered feedstocks by two oleaginous red yeasts. Bioresour Technol. 2019; 286:121365. doi:10.1016/j.biortech.2019.121365.
30. Yaegashi J, Kirby J, Ito M, Sun J, Dutta T, Mirsiaghi M, et al. *Rhodosporidium toruloides*: a new platform organism for conversion of lignocellulose into terpene biofuels and bioproducts. Biotechnol Biofuels. 2017; 10:241. doi:10.1186/s13068-017-0927-5.
31. Zhuang X, Kilian O, Monroe E, Ito M, Tran-Gymfi M B, Liu F, et al. Monoterpene production by the carotenogenic yeast *Rhodosporidium toruloides*. Microb Cell Fact. 2019; 18:54. doi:10.1186/s12934-019-1099-8.
32. Abramson M, Shoseyov O, Shani Z. Plant cell wall reconstruction toward improved lignocellulosic production and processability. Plant Sci. 2010; 178:61-72. doi:10.1016/j.plantsci.2009.11.003.
33. Xie M, Muchero W, Bryan A C, Yee K, Guo H-B, Zhang J, et al. A 5-Enolpyruvylshikimate 3-Phosphate Synthase Functions as a Transcriptional Repressor in *Populus*. Plant Cell. 2018; 30:1645-60. doi:10.1105/tpc.18.00168.
34. Dou C, Marcondes W F, Djaja J E, Bura R, Gustafson R. Can we use short rotation coppice poplar for sugar based biorefinery feedstock? Bioconversion of 2-year-old poplar grown as short rotation coppice. Biotechnol Biofuels. 2017; 10:144. doi:10.1186/s13068-017-0829-6.
35. ASTM Standard D-1655-19. In: Standard Specification for Aviation Turbine Fuels. West Conshohocken, Pa.: ASTM International; 2019.
36. Poling B E, Prausnitz J M, O'Connell J P. The Properties of Gases and Liquids. 5th edition. New York: McGraw-Hill; 2001.
37. Design Institute for Physical Properties of American Institute of Chemical Engineers. DIPPR 801. Website of: aiche.org/dippr. Accessed 4 Nov. 2019.
38. Ely J F, Hanley H J M. Prediction of transport properties. 1. Viscosity of fluids and mixtures. Ind Eng Chem Fund. 1981; 20:323-32. doi:10.1021/i100004a004.
39. Pedersen K S, Fredenslund A, Christensen P L, Thomassen P. Viscosity of crude oils. Chem Eng Sci. 1984; 39:1011-6. doi:10.1016/0009-2509(84)87009-8.
40. Pedersen K S, Fredenslund A. An improved corresponding states model for the prediction of oil and gas viscosities and thermal conductivities. Chem Eng Sci. 1987; 42:182-6. doi:10.1016/0009-2509(87)80225-7.
41. Harvey B. High Density Renewable Fuels From Zizaenes. 2019.
42. Edwards J T. Reference Jet Fuels for Combustion Testing. 2017.
43. Marrero J, Gani R. Group-contribution based estimation of pure component properties. Fluid Phase Equilib. 2001; 183-184:183-208. doi:10.1016/S0378-3812(01)00431-9.
44. Agrawal P M, Rice B M, Zheng L, Thompson D L. Molecular dynamics simulations of hexahydro-1,3,5-trinitro-1,3,5-s-triazine (RDX) using a combined Sorescu-Rice-Thompson AMBER force field. J Phys Chem B. 2006; 110:26185-8. doi:10.1021/jp065241t.
45. Agrawal P M, Rice B M, Thompson D L. Molecular dynamics study of the melting of nitromethane. J Chem Phys. 2003; 119:9617-27. doi:10.1063/1.1612915.
46. Kosir S T, Behnke L, Heyne J S, Stachler R D, Flora G, Zabarnick S, et al. Improvement in Jet Aircraft Operation with the Use of High-Performance Drop-in Fuels. In: AIAA Scitech 2019 Forum. Reston, Va.: American Institute of Aeronautics and Astronautics; 2019. doi:10.2514/6.2019-0993.
47. Coradetti S T, Pinel D, Geiselman G M, Ito M, Mondo S J, Reilly M C, et al. Functional genomics of lipid metabolism in the oleaginous yeast *Rhodosporidium toruloides*. elife. 2018; 7. doi:10.7554/eLife.32110.
48. Moreton R S. Physiology of lipid accumulation yeast. In: Single cell oil. London: Longman; 1988. p. 1-32.
49. Montet D, Ratomahenina R, Galzy P, Pina M, Graille J. A study of the influence of the growth media on the fatty acid composition in *Candida lipolytica* diddens and lodder. Biotechnol Lett. 1985; 7:733-6. doi:10.1007/BF01032285.
50. Papanikolaou S, Chevalot I, Komaitis M, Aggelis G, Marc I. Kinetic profile of the cellular lipid composition in an oleaginous *Yarrowia lipolytica* capable of producing a cocoa-butter substitute from industrial fats. Antonie Van Leeuwenhoek. 2001; 80:215-24.
51. Papanikolaou S, Galiotou-Panayotou M, Chevalot I, Komaitis M, Marc I, Aggelis G. Influence of glucose and saturated free-fatty acid mixtures on citric acid and lipid production by *Yarrowia lipolytica*. Curr Microbiol. 2006; 52:134-42. doi:10.1007/s00284-005-0223-7.
52. Wehrs M, Gladden J M, Liu Y, Platz L, Prahl J-P, Moon J, et al. Sustainable bioproduction of the blue pigment indigoidine: Expanding the range of heterologous products in *R. toruloides* to include non-ribosomal peptides. Green Chem. 2019. doi:10.1039/C9GC00920E.
53. Yoon S H, Rhim J W, Choi S Y, Ryu D D Y, Rhee J S. Effect of Carbon and Nitrogen Sources on Lipid Production of *Rhodotorula gracilis*. Journal of fermentation technology. 1982; 60:243-6.

54. Bicho P A, Runnals P L, Cunningham J D, Lee H. Induction of Xylose Reductase and Xylitol Dehydrogenase Activities in *Pachysolen tannophilus* and *Pichia stipitis* on Mixed Sugars. Appl Environ Microbiol. 1988; 54:50-4.
55. Lee H. Reversible inactivation of d-xylose utilization by d-glucose in the pentose-fermenting yeast *Pachysolen tannophilus*. FEMS Microbiol Lett. 1992; 92:1-4. doi: 10.1111/j.1574-6968.1992.tb05224.x.
56. Wedlock D N, James A P, Thornton R J. Glucose-negative Mutants of *Pachysolen tannophilus*. MICROBIOLOGY. 1989; 135:2019-26. doi:10.1099/00221287-135-7-2019.
57. Dashtban M, Wen X, Bajwa P K, Ho C-Y, Lee H. Deletion of hxk1 gene results in derepression of xylose utilization in *Scheffersomyces stipitis*. J Ind Microbiol Biotechnol. 2015; 42:889-96. doi:10.1007/s10295-015-1614-9.
58. Stein S E, Brown R L. Estimation of normal boiling points from group contributions. J Chem Inf Model. 1994; 34:581-7. doi:10.1021/ci00019a016.
59. Joback K G, Reid R C. Estimation of pure-component properties from group-contributions. Chem Eng Commun. 1987; 57:233-43. doi:10.1080/00986448708960487.
60. Irikura K K. THERMO.PL. Computer software. National Institute of Standards and Technology; 2002.
61. Becke A D. Density-functional thermochemistry. III. The role of exact exchange. J Chem Phys. 1993; 98:5648. doi:10.1063/1.464913.
62. Lee C, Yang W, Parr R G. Development of the Colle-Salvetti correlation-energy formula into a functional of the electron density. Phys Rev, B Condens Matter. 1988; 37:785-9. doi:10.1103/PhysRevB.37.785.
63. Process Systems Enterprise. Multiflash. Computer software. Process Systems Enterprise; 1997.
64. Edwards J T. Reference jet fuels for combustion testing. In: 55th AIAA Aerospace Sciences Meeting. Reston, Va.: American Institute of Aeronautics and Astronautics; 2017. doi:10.2514/6.2017-0146.
65. Montgomery J A, Frisch M J, Ochterski J W, Petersson G A. A complete basis set model chemistry. VII. Use of the minimum population localization method. J Chem Phys. 2000; 112:6532-42. doi:10.1063/1.481224.
66. Frisch M J, Trucks G W, Schlegel H B, Scuseria G E, Robb M A, Cheeseman J R, et al. GAUSSIAN09. Computer software. Wallingford, Conn.: Gaussian, Inc.; 2016.
67. Ham T S, Dmytriv Z, Plahar H, Chen J, Hillson N J, Keasling J D. Design, implementation and practice of JBEI-ICE: an open source biological part registry platform and tools. Nucleic Acids Res. 2012; 40:e141. doi: 10.1093/nar/gks531.
68. Abbott E P, Ianiri G, Castoria R, Idnurm A. Overcoming recalcitrant transformation and gene manipulation in Pucciniomycotina yeasts. Appl Microbiol Biotechnol. 2013; 97:283-95. doi:10.1007/s00253-012-4561-7.
69. Zhang S, Skerker J M, Rutter C D, Maurer M J, Arkin A P, Rao C V. Engineering *Rhodosporidium toruloides* for increased lipid production. Biotechnol Bioeng. 2016; 113: 1056-66. doi:10.1002/bit.25864.
70. Li C, Knierim B, Manisseri C, Arora R, Scheller H V, Auer M, et al. Comparison of dilute acid and ionic liquid pretreatment of switchgrass: Biomass recalcitrance, delignification and enzymatic saccharification. Bioresour Technol. 2010; 101:4900-6. doi:10.1016/j.biortech.2009.10.066.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

One-Pot Conversion of Poplar Biomass into High-Energy Density Tricyclic Sesquiterpene Jet Fuel Blend Exponential population growth and environmental concern has created a global interest to incorporate renewable energy as a long term solution. In an effort to decarbonize sectors, road transportation has increasing renewable energy options through electricity, leaving less accessible transportation, planes, to explore other options such as bioderived jet fuel. Specific energy and energy density are important in determining alternative-fuel viability as increased values enable further travel distance before refueling. Sesquiterpenes has been identified as a next-generation jet fuel alternative and production of energy-dense terpene biofuels from lignocellulosic biomass is a promising route to sustainable fuels. Therefore, an optimized one-pot ionic liquid (IL) treatment of poplar biomass is combined with sugar-to-fuel conversion of the tricyclic sesquiterpenes epi-isozizaene and prespatane by versatile basidiomycete, *Rhodosporidium toruloides*. To demonstrate production from renewable carbon sources and access process scalability prespatane is produced in 2 L reactors, reaching 1.17 g/L in one-pot poplar hydrolysate. Additionally, the theoretical fuel properties as well as their hydrogenated states is examined and compare them to Jet A and the existing alternative, farnasene. The findings indicate that both epi-isozizaene and prespatane will be attractive blending options in current jet fuel (Jet A) or other lower density renewable jet fuels. This represents the first heterologous production of prespatane and epi-isozizaene in *R. toruloides*, thus extending the range of sustainable bioderived jet fuel blending options. These results highlight the potential of *R. toruloides* for the sustainable and scalable production of bioderived jet fuel blends, with the first reporting of prespatane as an alternative jet fuel.

Herein is described the calculation of theoretical fuel properties of epi-isozizaene and prespatane indicate their potential suitability for use in jet fuel blends. Incorporating lignocellulosic biomass for bioconversion is advantageous because it is the most abundant renewable carbon-source after $CO_2$ and is thus considered an ideal feedstock for the sustainable production of bioproducts and bioenergy (Ragauskas et al. 2006). Generation of jet fuels from lignocellulosic biomass is potentially the best possible circumstance for reducing dependence on petroleum, mitigating greenhouse gas emissions (Rye et al. 2010) and increasing domestic energy independence (Baral et al. 2019). A microbial platform for conversion of lignocellulosic biomass into fuels offers product consistency suitable for use as drop-in components to fuel blendstocks (N. R. Baral et al. 2019; N. Baral et al. 2019).

The oleaginous yeast, *Rhodosporidium toruloides* (also known as *Rhodotorula toruloides* (Wang et al. 2015)), has previously been engineered to produce heterologous isoprenoids from lignocellulosic hydrolysates generated from various plant feedstocks (Sundstrom et al. 2018; Rodriguez et al. 2019; Yaegashi et al. 2017; Zhuang et al. 2019). One-pot ionic liquid (IL) pretreatment and saccharification offers an efficient, low cost process for conversion of biomass into fuels and has been previously employed to generate the biofuel candidate bisabolene in *R. toruloides* from a sorghum feedstock (Sundstrom et al. 2018). Poplar is explored as a feedstock for one-pot conversion to sesquiterpenes as its diffuse-porous wood and low to moderate specific gravity make it good for biochemical conversion (Abramson et al. 2010; Xie et al. 2018). Woody poplar is adaptable to various climates, is easily regenerated by coppicing and has the potential to provide a low-cost feedstock for biorefineries when grown in various scenarios such as short rotation coppice (Dou et al. 2017).

The theoretical jet fuel properties of epi-isozizaene, prespatane, and their hydrogenated states are analyzed and identified for the potential of being high performance molecules. This description represents the first to produce epi-isozizaene in a basidiomycete, and are also the first to produce prespatane as a potential jet fuel blend in any yeast. Furthermore, the development of the first scalable one-pot process comprising poplar feedstock, IL-pretreatment, saccharification, and fermentation is reported and this demonstrates the potential of *R. toruloides* as a robust host to convert poplar hydrolysate into jet fuel blend candidates.

Results and Discussion

Comparison of Predicted Fuel Properties of Tricyclic Sesquiterpenes with Jet A

Specific physical properties are used to determine the specification and impact performance of jet fuels, such as boiling point, viscosity, melting point, energy density, and specific energy. These physical properties, and their acceptable ranges are governed by ASTM D1655-19 "Standard Specification for Aviation Turbine Fuels" (Anon 2019). In this test method, liquid density is measured at 15° C., and has an acceptable range of 775 to 840 kg/m$^3$. The Rackett equation, which is outlined in the Materials and methods section, is a really good theoretical predictor of liquid density. Poling, Prausnitz and O'Connell compared the accuracy of the Rackett equation against 225 experimentally derived density measurements (Poling et al. 2001). Their analysis showed that the Rackett equation gave an average deviation of 2.6%. Applying the Rackett equation to prespatane and saturated prespatane, at 15° C., yields 900 and 966 kg/m$^3$, respectively. Similarly, the Rackett equation gives 1000 and 963 kg/m$^3$ as calculated results for Epi-isozizaene and saturated Epi-isozizaene, respectively. For prespatane, the saturation of the appended propene group increases the liquid density. The opposite effect is observed for the saturation of epi-isozizaene. These apparently conflicting results may be due to the saturation of an appendage side group double bond vs. the saturation of an internal cyclic double bond. Liquid density data from DIPPR, for pinane and α-pinene at 15° C. show similar trends to our work (pinane=861, and α-pinene=875.0 kg/m$^3$), that is that the saturation of a cyclic double bond decreases the liquid density.

Figure 5A:
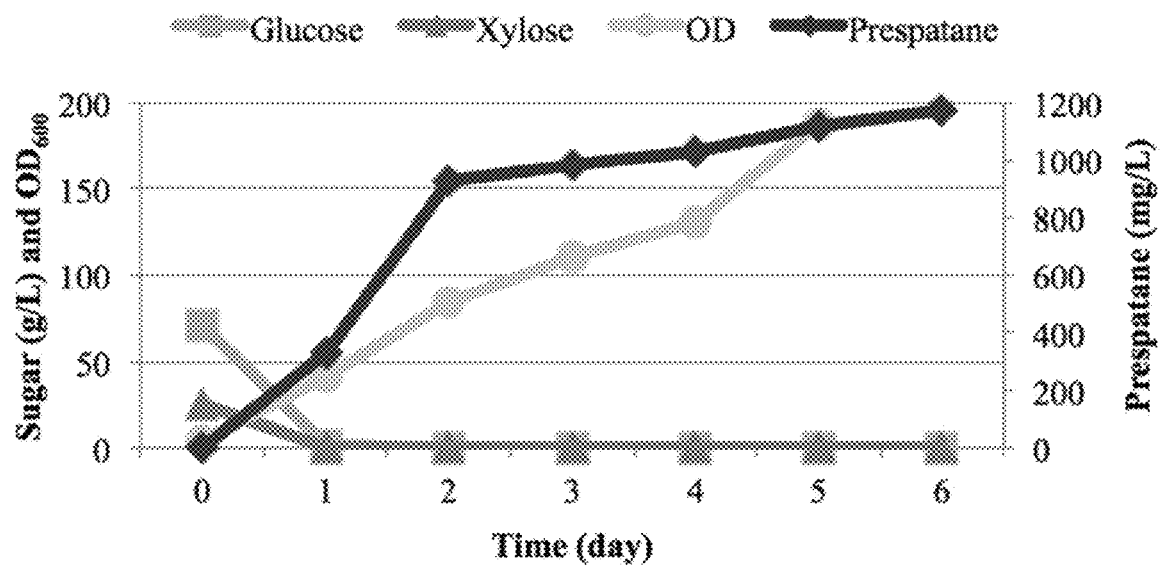
FIG. 5A. Fermentation results. Sugar concentrations, $OD_{600}$, and prespatane titer of bioreactor runs with PPS5 in filtered hydrolysate from batch 3.

There are two corresponding states methods available for calculating accurate viscosities, SUPERTRAPP, and Pedersen (Ely and Hanley 1981; Pedersen et al. 1984; Pedersen and Fredenslund 1987). Both have been used extensively, and both often give accurate viscosities. However, given that it is hard to tell which method will be the most reliable for this application, several molecules are screened, against viscosity data available in DIPPR (Design Institute for Physical Properties of American Institute of Chemical Engineers n.d.). These molecules will be used later in the development of a blend model, but here, they are being screened to access the relative reliability of both viscosity methods. The screening results are shown in Table 5. For each compound, the % AAD (Absolute Average Deviation), for each method is displayed. It is clear, that SUPERTRAPP works really well, with most % AADs well below 10. In contrast, the Pedersen method yields reliable results sometimes, but many times its predictions are off. Indeed, many of the predictions made by the Pedersen method are 25-60% off. Based on this data, the SUPERTRAPP method was used to model the viscosity of prespatane, saturated prespatane, epi-isozizaene, and saturated isozizaene. These viscosity results are presented in FIG. 6. Based on the ASTM D1655-19 standard test method, the viscosity of Jet A, at –20° C., must not exceed 8 mm$^2$/s (Anon 2019). In addition, there are extended requirements outlined in ASTM D1655-19, which are applicable to fuels containing Co-hydroprocessed Esters, and Fatty Acids. According to these requirements, at –40° C., the viscosity cannot exceed 12 mm$^2$/s. This requirement is commonly included in typical Jet A requirements, and thus will also be enforced here (Anon 2019). Based on the data presented in FIG. 6, both saturated and unsaturated sesquiterpenes meet these requirements. The isozizaenes have a much lower viscosity than the prespatanes, indicating a more flexible cyclic ring system able to accommodate arrangements suitable for faster flow. Saturated prespatane shows somewhat lower viscosity than prespatane. This may be due to the natural hindered rotation of double bonds. It is important to note that there are no reported viscosity measurements for any of the molecules of interest in this paper. However, a patent filed by Harvey in 2019 investigated the viscosity of zizaene blends (Harvey 2019). Specifically, these blends contained ziaene, epi-isozizaene, and prezizaene, and he also included blends in which these molecules were fully saturated. Additionally, in an effort to increase the net heat of combustion, these blends were dimerized. At –20° C., his viscosity measurements are much higher than what is reported here. This is likely due to the dimerization of sesquiterpenes, but may also be due to the formation of waxes, or emulsions, which are not taken into account by corresponding states methods.

| Chemical name | Temperature Range ° C. | Number of points | % AAD, SUPERTRAPP | % AAD Pedersen |
|---|---|---|---|---|
| Alkylbenzenes | | | | |
| Ethylbenzene | –40 to 40 | 18 | 3.8 | 36.2 |
| Propylbenzene | –40 to 40 | 18 | 3.3 | 38.6 |
| Butylbenzene | 5 to 40 | 9 | 1.8 | 41.5 |
| Pentylbenzene | 10 to 40 | 8 | 1.8 | 41.6 |
| Hexylbenzene | 10 to 40 | 8 | 4.5 | 52.1 |
| Alkylnaphthalenes | | | | |
| 1-ethylnaphthalene | 0 to 40 | 10 | 5.4 | 59.2 |
| Cycloaromatics | | | | |
| 1-ethyltetralin | 0 to 40 | 10 | 7.8 | 21.7 |
| Iso-Paraffins | | | | |
| 2-methyloctane | 0 to 40 | 10 | 7.4 | 3.1 |
| 2-methylnonane | 0 to 40 | 10 | 32.1 | 34.5 |
| 2-methyldecane | 0 to 40 | 10 | 1.4 | 4.1 |
| 2-methylundecane | 0 to 40 | 10 | 3.0 | 6.1 |
| 2-methyldodecane | –3 to 40 | 10 | 3.4 | 10.5 |
| 2-methyltridecane | –3 to 40 | 10 | 3.1 | 16.6 |
| 2-methyltetradecane | –3 to 40 | 10 | 8.7 | 38.1 |
| 2-methylpentadecane | 0 to 40 | 10 | 18 | 58.6 |

-continued

| Chemical name | Temperature Range ° C. | Number of points | % AAD, SUPERTRAPP | % AAD Pedersen |
|---|---|---|---|---|
| N-Paraffins | | | | |
| Nonane | −40 to 40 | 18 | 1.9 | 5.7 |
| Decane | −28 to 40 | 15 | 1.6 | 6.1 |
| Undecane | 8 to 40 | 11 | 1.1 | 4.2 |
| Dodecane | −8 to 40 | 11 | 0.8 | 8.8 |
| Tridecane | 0 to 40 | 10 | 0.3 | 11.8 |
| Tetradecane | 12 to 40 | 7 | 1.1 | 18.8 |
| Pentadecane | 22 to 40 | 5 | 2.3 | 25.8 |
| Monocycloparaffins | | | | |
| propylcyclohexane | −40 to 40 | 18 | 7.8 | 28.7 |
| butylcyclohexane | 22 to 40 | 5 | 1.4 | 15.7 |
| pentylcyclohexane | −3 to 40 | 10 | 3.0 | 5.9 |
| hexylcydohexane | −3 to 40 | 10 | 46.0 | 10.2 |
| heptylcyclohexane | −3 to 40 | 10 | 34.1 | 14.4 |
| octylcyclohexane | 2 to 40 | 9 | 29.6 | 25.6 |
| nonylcyclohexane | −3 to 40 | 10 | 34.5 | 29.2 |
| Dicycloparaffins | | | | |
| Cis-decalin | −28 to 40 | 15 | 2.2 | 28.4 |

Figure 7:
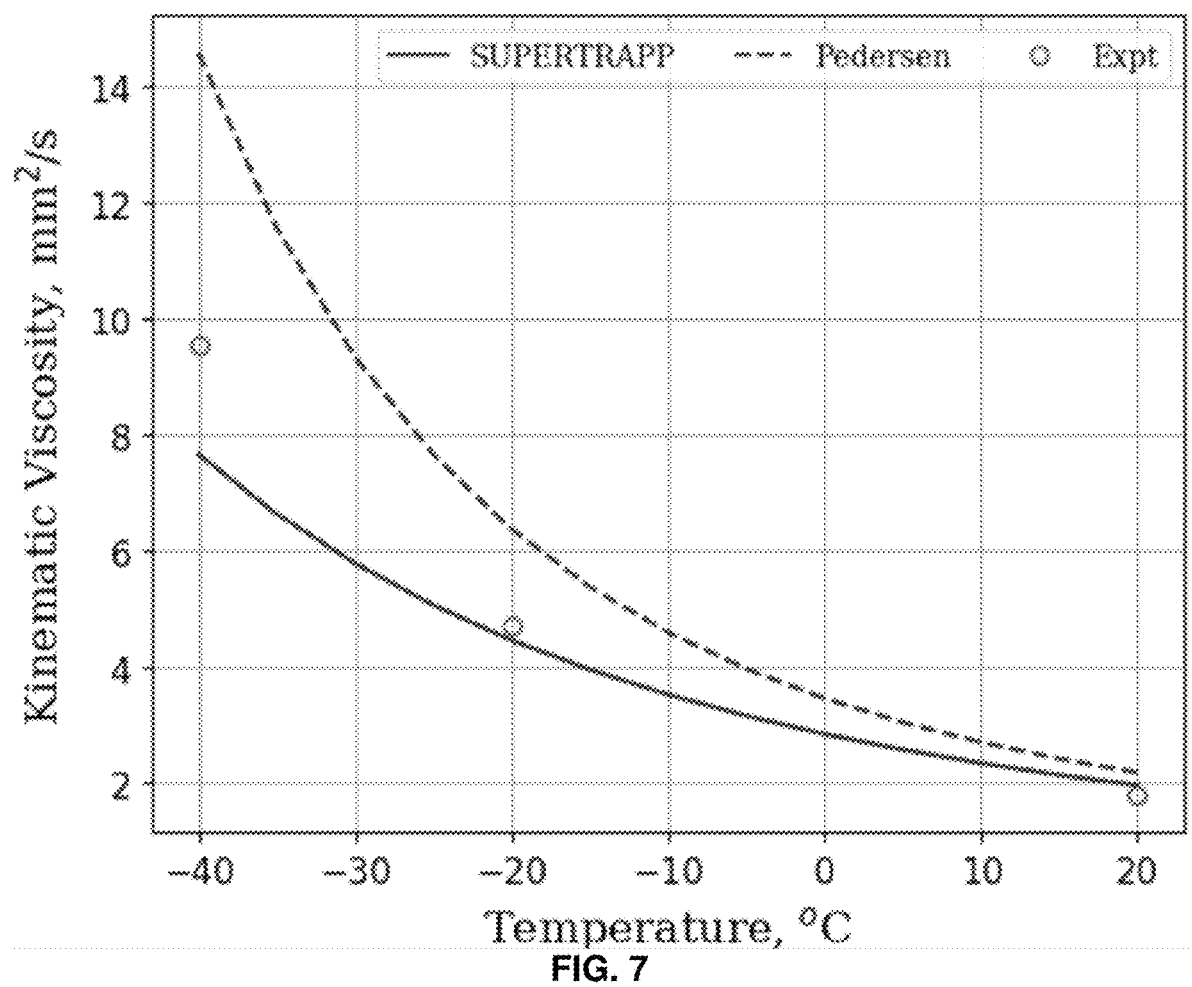
FIG. 7. Validation of a viscosity model for Jet A. Solid blue curve is the results using the SUPERTRAPP method, dashed blue line is the results using the Pedersen method, and the red open circles are experimental viscosities.

In order to understand blending behavior, a blend model of a typical Jet A fuel is developed. The details of how this model was developed is given in the MATERIALS AND METHODS section however, as noted in the previous paragraph, the components which went into the blend model are evaluated against viscosity data in the DIPPR database (Design Institute for Physical Properties of American Institute of Chemical Engineers) FIG. 7 shows a comparison of the modeled viscosity curve, for the blend model, against the available experimental viscosity data (Edwards 2017). Two viscosity curves are plotted, one using the SUPERTRAPP method, and the other using the Pedersen method. The data shows that the SUPERTRAPP method does a much better job of estimating the viscosity, than the Pedersen method. At 20, −20, and −40° C., the SUPERTRAPP method has a % error of 9.25, 5.26, and 19.78. These errors are in the range of what the typical error is for SUPERTRAPP, and it shows that the viscosity model for Jet A is reliable.

Figure 8A:
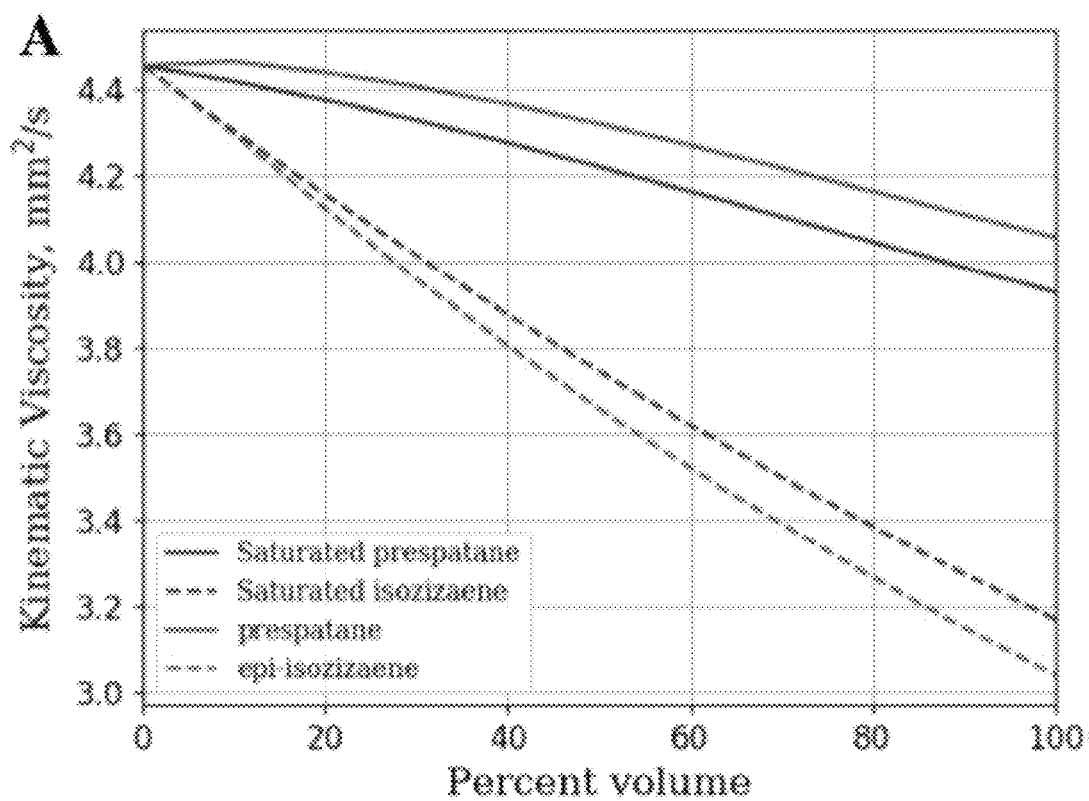
FIG. 8A. Viscosity blending behavior of prespatane, epi-isozizaene, saturated prespatane, and saturated epi-isozizaene at −20° C.
Figure 8B:
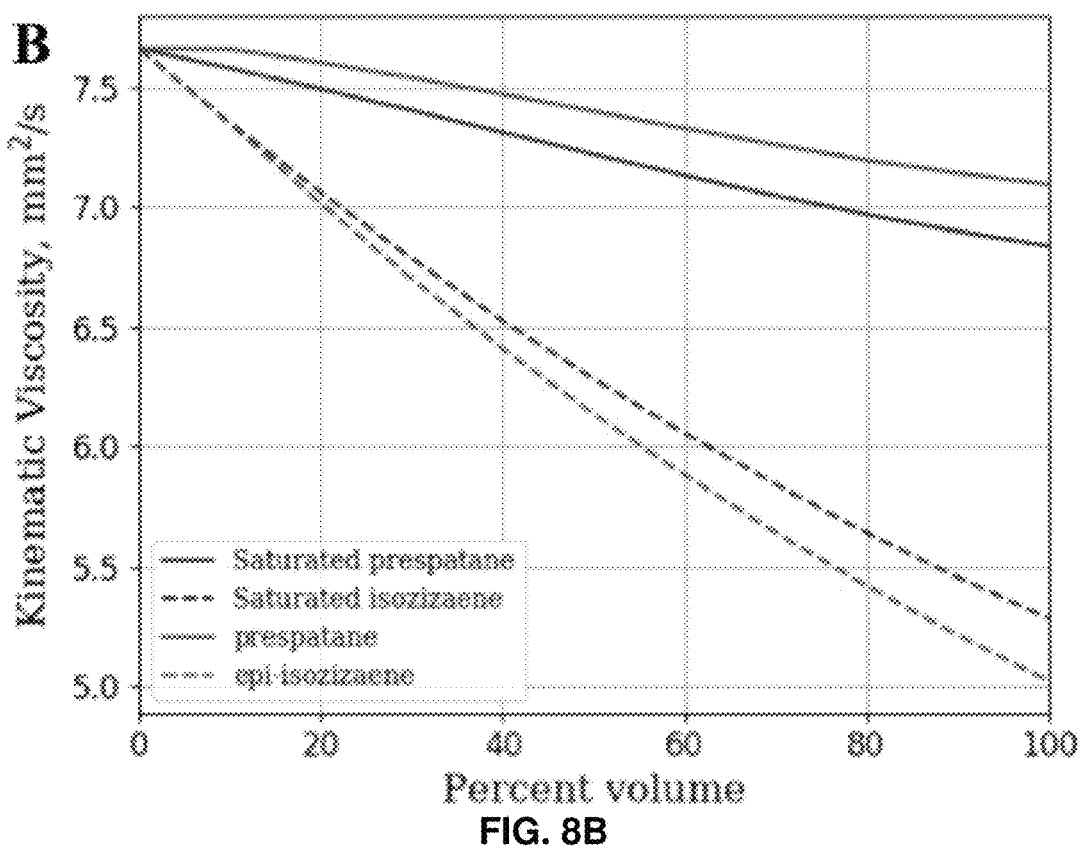
FIG. 8B. Viscosity blending behavior of prespatane, epi-isozizaene, saturated prespatane, and saturated epi-isozizaene at −40° C.
Figure 9:
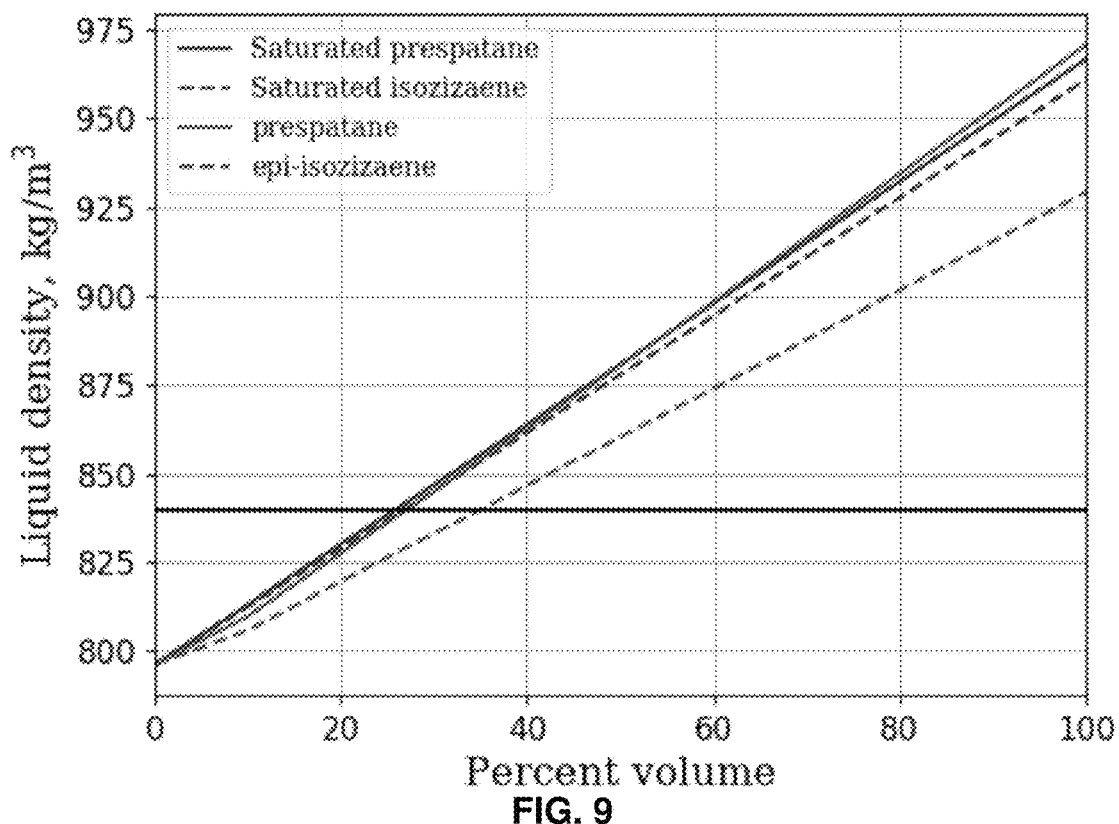
FIG. 9. Liquid density blending behavior of prespatane, epi-isozizaene, saturated prespatane, and saturated isozizaene at 15° C.
Figure 10:
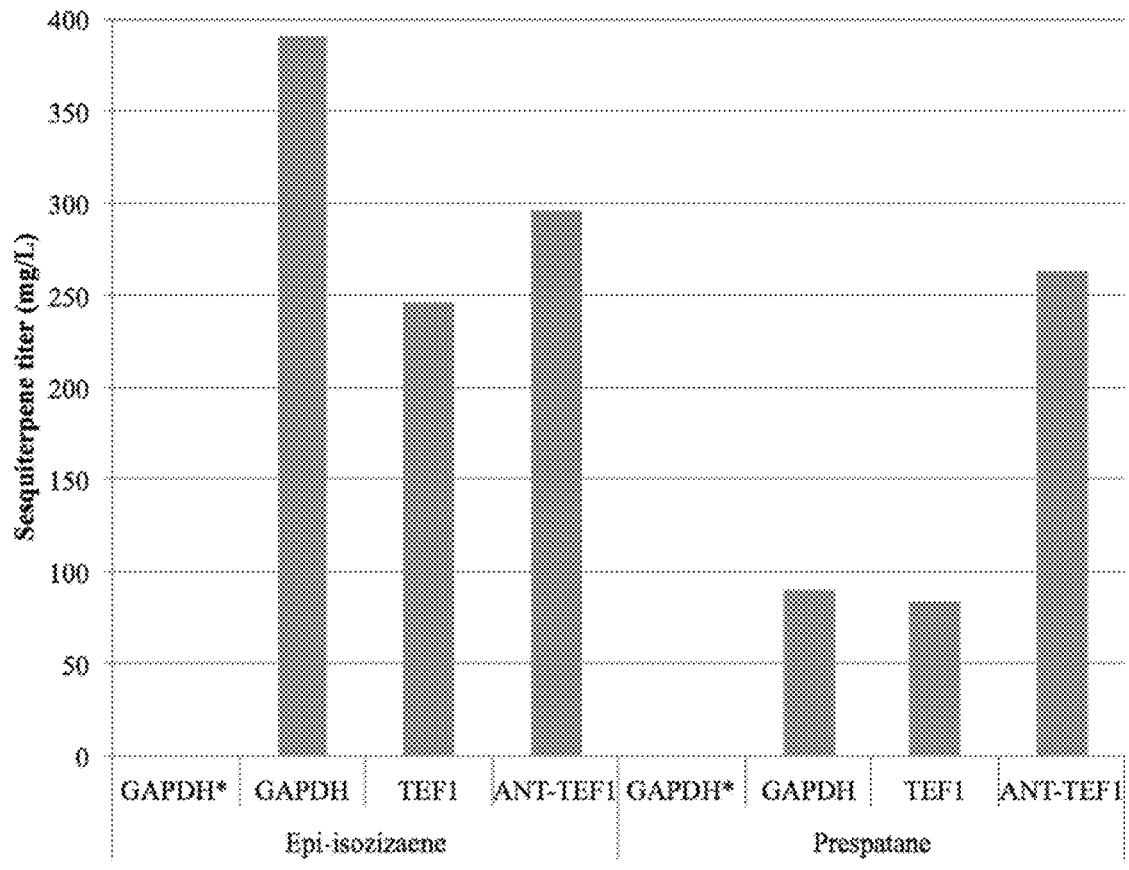
FIG. 10. Sesquiterpene titer of highest producing strain for each construct. Cultures are grown in $YP_{100}$ with a 20% dodecane overlay. At day 7, the dodecane overlay is sampled and analyzed for epi-isozizaene and prespatane. Sample names are represented by their perspective promoters GAPDH, TEF1, and two promoter construct, ANT-TEF1. Native gene synthase is represented by *.
Figure 11A:
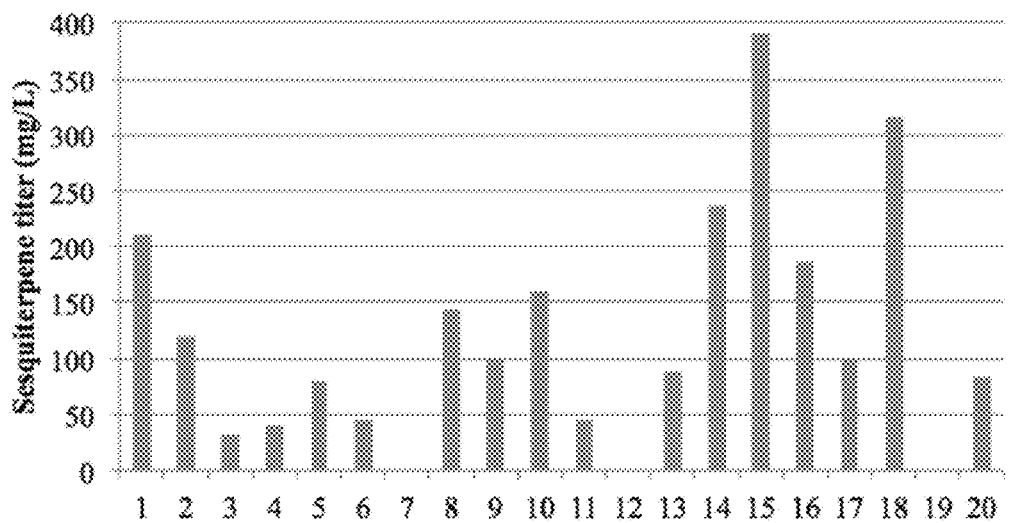
FIG. 11A. Sesquiterpene titer of 20 *R. toruloides* transformants with construct 2. Cultures were grown in $YP_{100}$ with a 20% dodecane overlay. At day 7, the dodecane overlay was sampled and analyzed for epi-isozizaene and prespatane.
Figure 11B:
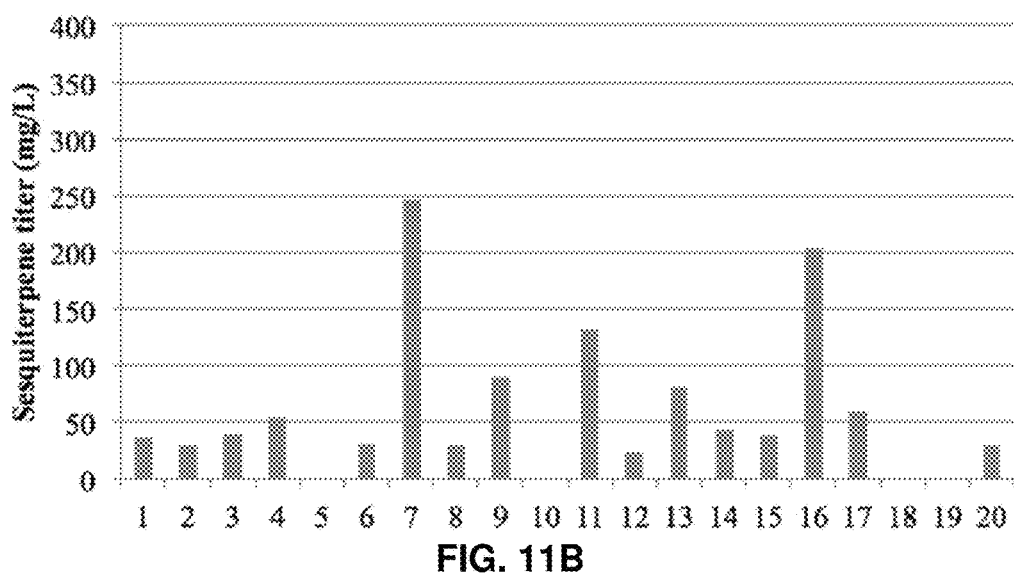
FIG. 11B. Sesquiterpene titer of 20 *R. toruloides* transformants with construct 3. Cultures were grown in $YP_{100}$ with a 20% dodecane overlay. At day 7, the dodecane overlay was sampled and analyzed for epi-isozizaene and prespatane.
Figure 11C:
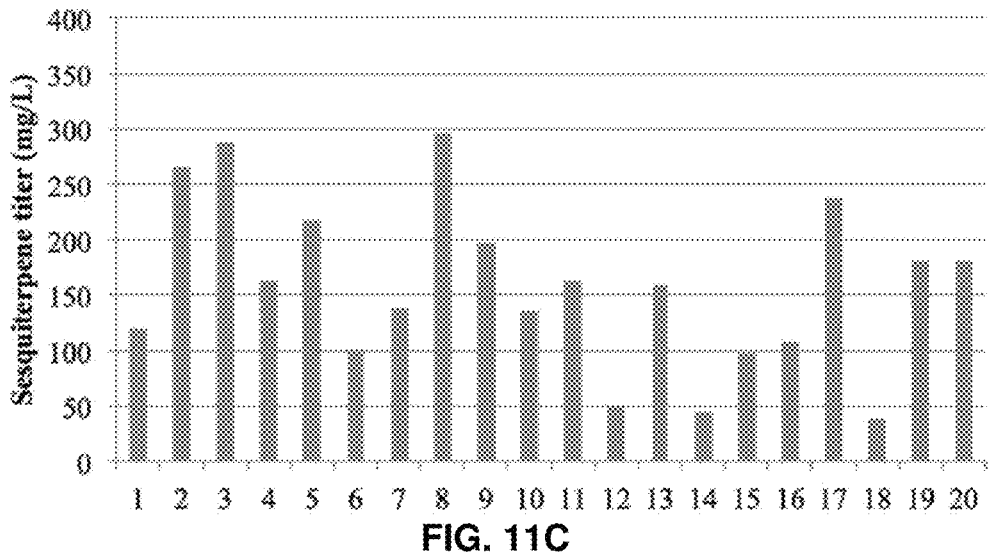
FIG. 11C. Sesquiterpene titer of 20 *R. toruloides* transformants with construct 4. Cultures were grown in $YP_{100}$ with a 20% dodecane overlay. At day 7, the dodecane overlay was sampled and analyzed for epi-isozizaene and prespatane.
Figure 11D:
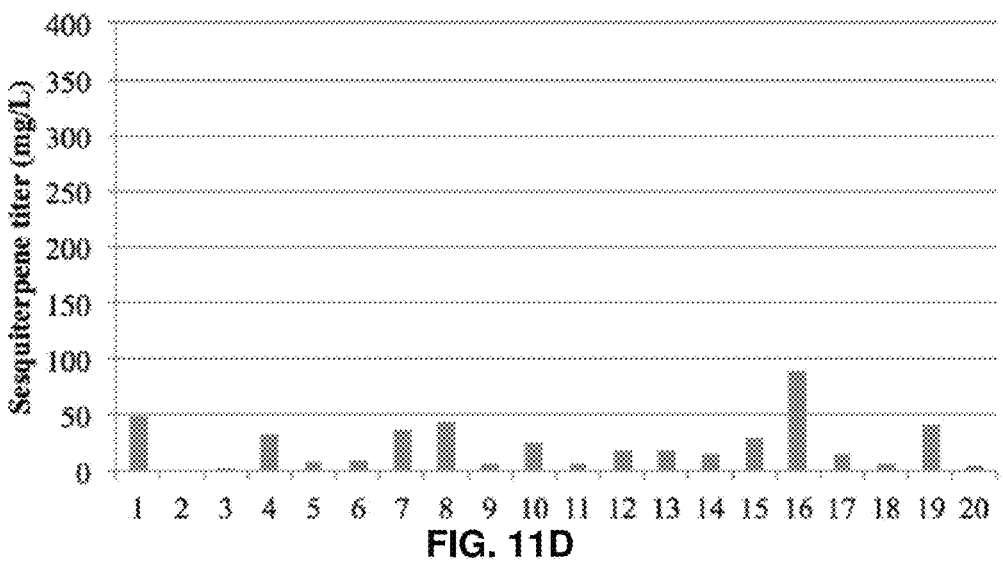
FIG. 11D. Sesquiterpene titer of 20 *R. toruloides* transformants with construct 6. Cultures were grown in $YP_{100}$ with a 20% dodecane overlay. At day 7, the dodecane overlay was sampled and analyzed for epi-isozizaene and prespatane.
Figure 11E:
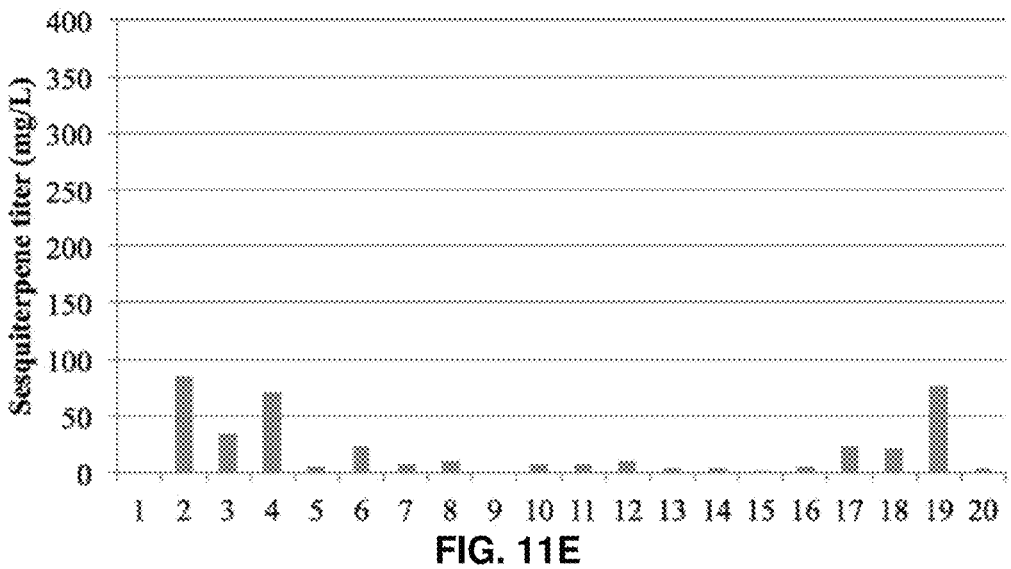
FIG. 11E. Sesquiterpene titer of 20 *R. toruloides* transformants with construct 7. Cultures were grown in $YP_{100}$ with a 20% dodecane overlay. At day 7, the dodecane overlay was sampled and analyzed for epi-isozizaene and prespatane.
Figure 11F:
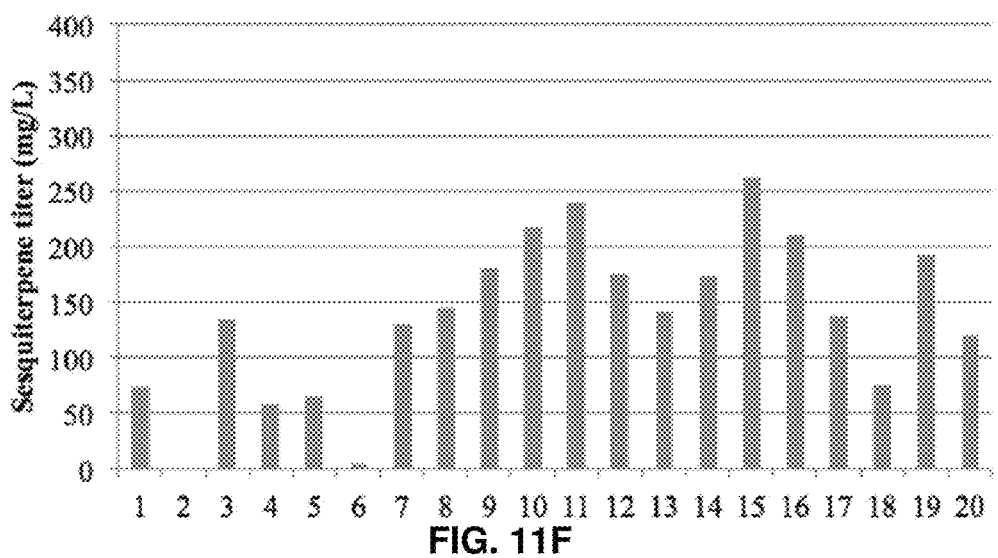
FIG. 11F. Sesquiterpene titer of 20 *R. toruloides* transformants with construct 8. Cultures were grown in $YP_{100}$ with a 20% dodecane overlay. At day 7, the dodecane overlay was sampled and analyzed for epi-isozizaene and prespatane.

With a model for Jet A in hand, estimates of the blending behavior of prespatane, epi-isozizaene, saturated prespatane, and saturated epi-isozizaene are carried out. These calculations focus on viscosity at −20, and −40° C., as well as liquid density at 15° C. FIGS. 8A and 8B show the results of this work. According to the data, all of these molecules decrease the viscosity of Jet A. Isozizaenes decrease the viscosity of Jet A faster than prespatanes, and there is little difference between saturated and unsaturated counterparts. While viscosity is not going to affect the degree with which blending can occur, liquid density will. The specification for liquid density, at 15° C., place an upper limit of 840 kg/m$^3$ on any aviation fuel. FIG. 9 shows that all molecules can be blended up to ~30% (by volume) before reaching this limit. A horizontal black line highlights this upper limit. Epi-isozizaene can be blended in the largest proportion, reaching the upper limit of 840 kg/m$^3$ just shy of a blend level of 40%.

The maximum acceptable melting point of an aviation fuel is −40° C. Marrero and Gani have developed a complex group contribution method that is capable of predicting the melting point of hydrocarbons (Marrero and Gani 2001). It includes an initial group contribution estimate followed by two successive correction terms that improve upon that initial melting point estimate. Tested over 1103 melting point data points, this method features a standard deviation of 25.34 K, and an absolute average error of 18.76 K. While not a perfect estimate of melting point, it is one of the best group contribution methods available to date. Table 1 highlights the melting points of prespatane, epi-isozizaene, saturated prespatane, and saturated isozizaene. The melting points of the unsaturated terpenes hover around 0° C., while saturated prespatane and isozizaene have melting points that are a bit higher. None of them meet the −40° C. threshold outlined by ASTM D1655-19 (Anon 2019), and none of them could be considered, by themselves, a competent aviation fuel. However, the melting point of a blend is a highly non-linear process, and the complex chemical interactions responsible for melting are not easily represented. Molecular Dynamics (MD) calculations, as an alternative approach to estimating melting points, are certainly possible, however, their errors are similar to the errors encountered by the group contribution used here (Agrawal et al. 2006; Agrawal et al. 2003).

TABLE 1

Relevant physical properties estimated for epi-isozizaene, prespatane, saturated isozizaene, and saturated prespatane.

| | Epi-isozizaene | Pres-patane | Saturated isozizaene | Saturated prespatane |
|---|---|---|---|---|
| Liquid density, kg/m$^3$ | 1000 | 900 | 963 | 966 |
| Boiling point, ° C. | 273.81 | 255.58 | 257.71 | 261.18 |
| Viscosity, mm$^2$/s, −20° C. | 3.04 | 4.05 | 3.17 | 3.93 |
| Viscosity, mm$^2$/s, −40° C. | 5.02 | 7.09 | 5.28 | 6.84 |
| Melting point, ° C. | −1.92 | 1.88 | 25.79 | 10.00 |
| Energy density, MJ/L | 39.25 | 41.42 | 40.69 | 41.46 |
| Specific energy, MJ/kg | 42.58 | 43.06 | 42.72 | 43.27 |

Energy density and specific energies are calculated using ab-initio Quantum Mechanics calculations, the specifics of which is written in the Materials and methods section. Table 1 shows the results of these calculations. The saturation of the double bonds found in prespatane and isozizaene cause both the specific energy and energy density to increase modestly. For saturated prespatane, its specific energy is just slightly above the median Jet A specific energy of 43.2 MJ/kg. However, its energy density of 41.46 MJ/L places it well above the Jet A median value of 34.9 MJ/L (Kosir et al. 2019). Saturated isozizaene, isozizaene, and prespatane all show similar trends. This increase in energy density is partly due to large liquid densities, and as a blend, these molecules should help to decrease the volume of fuel required to complete trips.

Strain Development and Optimization for Production of Epi-Isozizaene and Prespatane R. toruloides genomic DNA has an overall high GC-content of 62.93% (Coradetti et al. 2018), indicating that codon optimization may be particularly important for expression of heterologous genes. Indeed, the majority of studies describing heterologous biofuels production in R. toruloides employ codon optimized gene sequences to ensure effective expression (Yaegashi et al. 2017; Sundstrom et al. 2018; Rodriguez et al. 2019; Zhuang et al. 2019) and comparison to non-optimized has not yet been explored. Both codon-optimized and native versions of prespatane synthase from L. pacifica (native GC-content: 51%) and epi-isozizaene synthase from S. coelicolor A3(2) (native GC-content: 56%) are expressed in R. toruloides.

Codon optimization results in a 14% increase in GC-content for both genes. Rare codons for R. toruloides (those that occur below 20% of frequency expected if there was no codon bias; namely, ATA, CTA, TTA, AGA, and GTA) are present at relatively high frequencies both native genes. In the native EIZS gene, TTA (13.5%) and GTA (31.8%) are present at a much higher frequency than that in *R. toruloides* (0.8% and 4.3%, respectively). In the native PPS gene, ATA (23.5%), CTA (3.3%), TTA (13.3%), AGA (30%), and GTA (10%) are present at a higher frequency than that in *R. toruloides* (3.3%, 2.6%, 0.8%, 3.2%, and 4.3%, respectively).

A total of 8 constructs are transformed into *R. toruloides* using ATMT and 20 individual clones are selected from each transformation for initial screening. Overall, no prespatane or epi-isozizaene is detected in strains harboring native synthases (constructs 1 and 5, respectively). This indicates that codon-optimization might be necessary. Indeed, when the production from codon optimized versions is checked, it works with the median titer of epi-isozizaene at 94 mg/L (range, 390 mg/L) and prespatane at 25 mg/L (range, 263 mg/L) (FIG. 10, or 11A to 11F). Interestingly, highest epi-isozizaene production is observed using promoter GAPDH while prespatane production is highest using promoters ANT and TEF1. Other minor products are detected from both synthases (Table 4) on GC-MS.

| Molecule | Percentage (%) |
|---|---|
| A | |
| prespatane | 85.6 |
| bicyclo[4.3.0]nonane, 7-methylene-2,4,4-trimethyl-2-vinyl or (+)-valencene | 8.1 |
| γ-gurjunene | 3.7 |
| α-guaiene or α-selinene | 0.8 |
| γ-elemene | 0.7 |
| (+)-ledene | 0.6 |
| β-guaiene | 0.4 |
| viridiflorene | 0.1 |
| B | |
| epi-isozizaene | 92.4 |
| 26.85 Khusimene (=zizaene) | 3.7 |
| cedrene or (Z)-β-farnesene | 2.4 |
| α-cedrene | 0.5 |
| α-longipinene or 30.03 bisaboline ((E)-γ)) | 0.5 |
| farnesyl acetone | 0.5 |

Figure 2A:
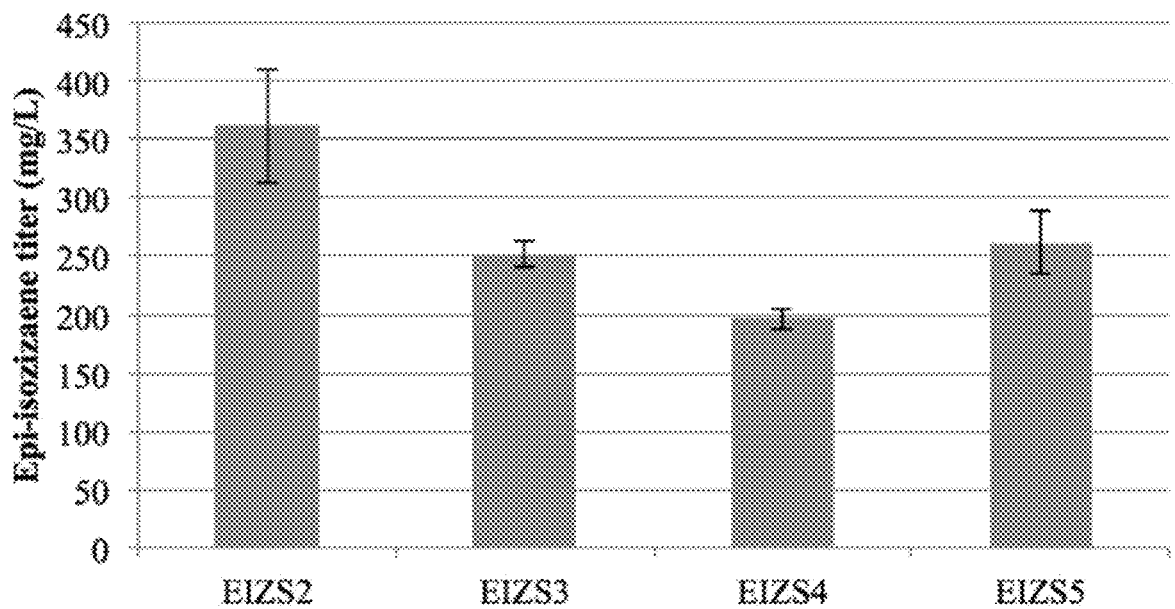
FIG. 2A. Sesquiterpene titer of highest producing R. toruloides clones. Epi-isozizaene titers grown in $YP_{100}$ with a 20% dodecane overlay. At day 7, the dodecane overlay is sampled and analyzed for epi-isozizaene and prespatane. (n=3, data shown as average±standard deviation, from a single experiment).
Figure 2B:
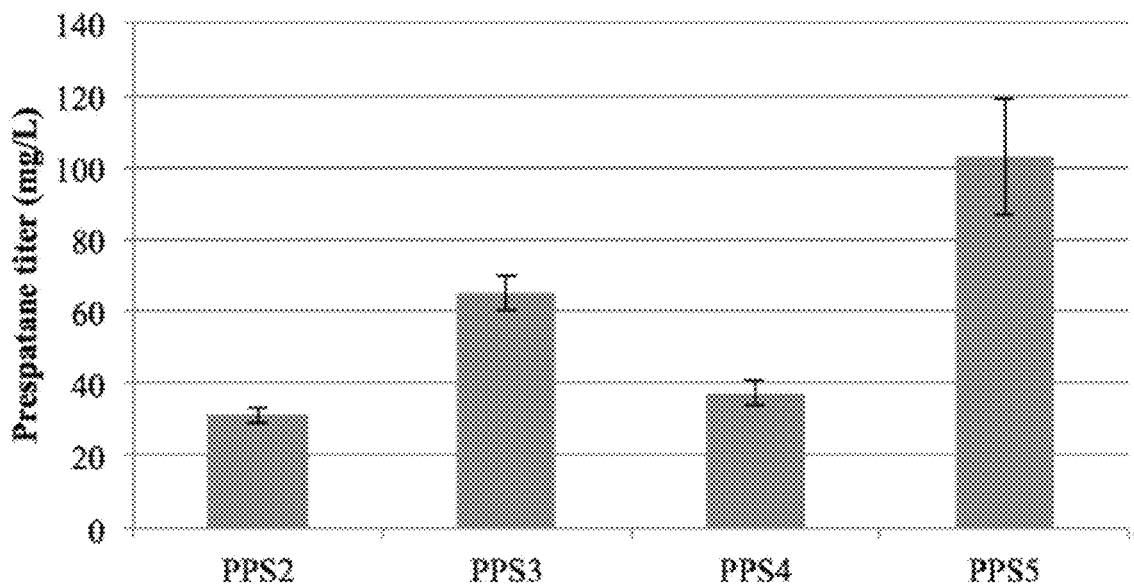
FIG. 2B. Sesquiterpene titer of highest producing R. toruloides clones. Prespatane titers grown in $YP_{100}$ with a 20% dodecane overlay. At day 7, the dodecane overlay is sampled and analyzed for epi-isozizaene and prespatane. (n=3, data shown as average±standard deviation, from a single experiment).

To assess if increasing the copy number of the heterologous gene improves production of the respective sesquiterpene, the highest producing clones for each construct with NAT resistance (e.g. GAPDH and double promoter ANT and TEF1, respectively) is transformed with the respective plasmid containing the HYG selection marker (TEF1) creating strains EIZS3, EIZS5, PPS3 and PPS5. Production is tested again in triplicate (FIGS. 2A and 2B).

After a second round of transformation, titers increase for all but one strain, EIZS2 (362±49 mg/L), as it remains the highest epi-isozizaene producer. However, the highest prespatane producing strain becomes PPS5 (JPUB_013541), as it produced 103±16 mg/L. The best producing strains are selected for further analysis on poplar hydrolysate.

Optimization of Poplar Hydrolysates Generation Using a One-Pot Approach

To improve the sustainability of biofuel production, hydrolysate from lignocellulosic biomass has been incorporated as a bioconversion resource. Previously, a one-pot ionic liquid pretreatment and saccharification method using sorghum biomass was developed and production of the sesquiterpene bisabolene was successfully demonstrated (Sundstrom et al. 2018). In comparison to sorghum, poplar has diffuse-porous wood and low to moderate specific gravity which makes it readily accessible for pretreatment and saccharification (Dou et al. 2017; Xie et al. 2018; Abramson et al. 2010).

Figure 14A:
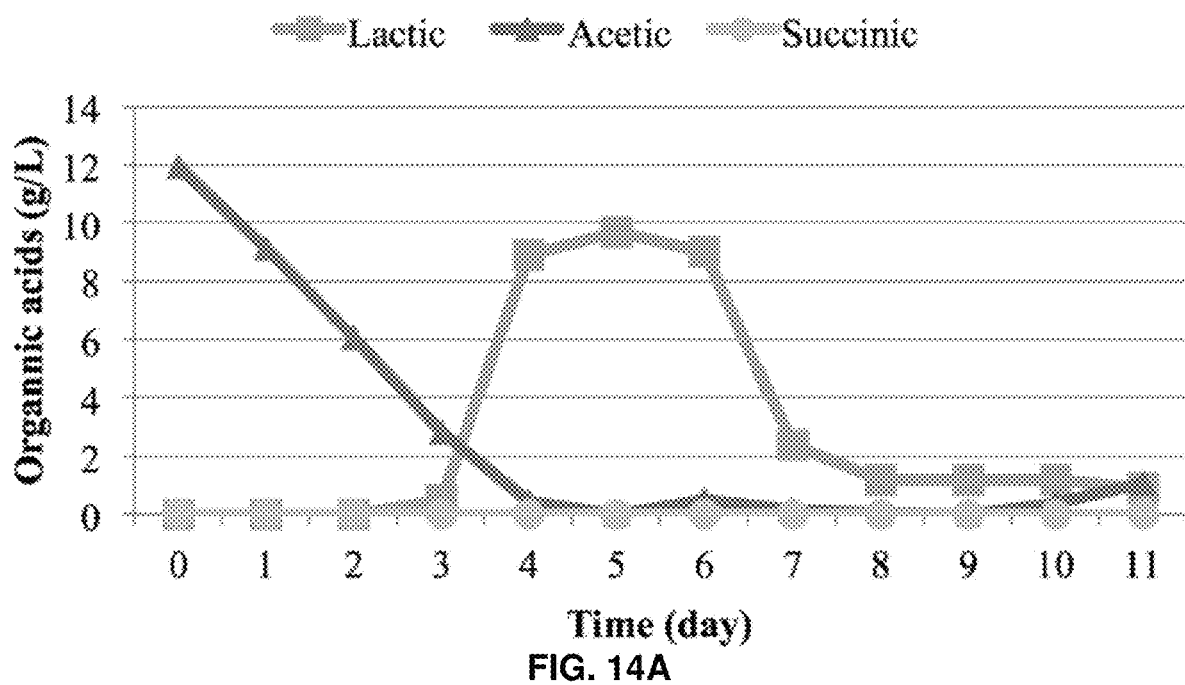
FIG. 14A. Fermentation results of PPS5 from unfiltered hydrolysate batch 3. Organic acids.

The woody biomass poplar is implemented to investigate its behavior and affect on the performance of *R. toruloides* epi-isozizaene and prespatane production strains. The pretreatment and saccharification process of poplar using IL is optimized in three consecutive rounds, using the Sundstrom process as basis for optimization (Table 3). Generally, lowering biomass loading while increasing duration of boiling during pretreatment results in an increase of sugars released from the biomass. Finally, changing the enzyme cocktail from CTec2/HTec2 to CTec3/HTec3 further improves the process leading to concentration of 77 g/L glucose and 26.6 g/L xylose (Table 3). In all cases, dense particle suspension is observed when poplar hydrolysate remained unfiltered (FIG. 14).

Figures 4A, 4B:
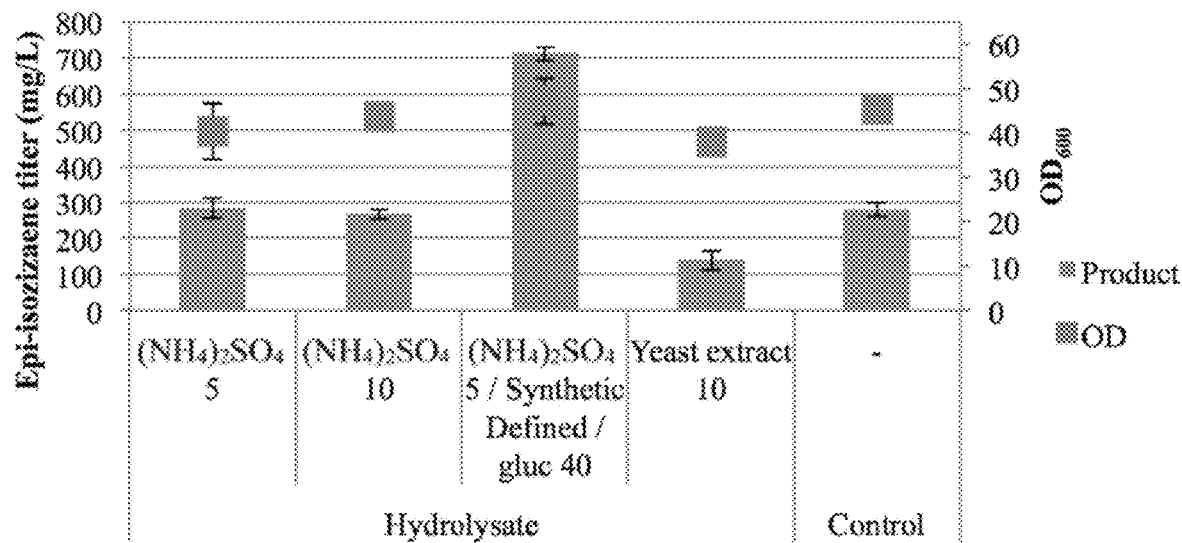
FIG. 4A. Nitrogen source supplementation comparisons in one-pot poplar hydrolysate. Epi-isozizaene titer and $OD_{600}$ of strain EIZS2 in filtered batch 1 poplar hydrolysate supplemented with various nitrogen sources and a 20% dodecane overlay. At day 7, the dodecane overlay is sampled and analyzed for epi-isozizaene. $(NH_4)_2SO_4$ 5 and 10, ammonium sulfate 5 g/L and 10 g/L; Synthetic Defined, Yeast Nitrogen Base without amino acids 6.7 g/L and CSM powder 0.79 g/L, pH adjusted to 7 with 2 M NaOH; gluc 40, glucose 40 g/L; Yeast extract 10, yeast extract 10 g/L; and Control, yeast extract 10 g/L, peptone 20 g/L, and glucose 100 g/L. (n=3, data shown as average±standard deviation, from a single experiment)
FIG. 4B. Nitrogen source supplementation comparisons in one-pot poplar hydrolysate. Percent utilization of sugar and yield per gram of sugar ($mg_{prespatane}/g_{glucose}$). $(NH_4)_2SO_4$ 5 and 10, ammonium sulfate 5 g/L and 10 g/L; Synthetic Defined, Yeast Nitrogen Base without amino acids 6.7 g/L and CSM powder 0.79 g/L, pH adjusted to 7 with 2 M NaOH; gluc 40, glucose 40 g/L; Yeast extract 10, yeast extract 10 g/L; and Control, yeast extract 10 g/L, peptone 20 g/L, and glucose 100 g/L. (n=3, data shown as average±standard deviation, from a single experiment)

Bench-Scale Optimization of Poplar Hydrolysates for Production of Jet Fuel Blend Candidates Nitrogen limitation is known to enhance accumulation of storage fat in oleaginous yeast (Moreton 1988; Montet et al. 1985; Papanikolaou et al. 2001; Papanikolaou et al. 2006). In addition, it has been shown that the source of nitrogen can have a significant effect on product formation as well as abiotic growth (Wehrs et al. 2019; Yoon et al. 1982). To test if this applies to our process, we supplement the hydrolysate obtained in batch 1 (glucose g/L: 46.3±2.1 and xylose g/L: 14.2±4.7) with four nitrogen source variations (FIGS. 4A and 4B) and quantified epi-isozizaene production using strain EIZS2 after one week of cultivation. Overall, $OD_{600}$ are similar, ranging from 37.9 to 47.1. Generally, supplementation with ammonium sulfate leads to higher epi-isozizaene production than 10 g/L yeast extract (139±26 mg/L), while no significant difference in production is observed for increased concentration of ammonium sulfate (284±29 mg/L and 267±14 mg/L epi-isozizaene for 5 and 10 g/L ammonium sulfate respectively) (FIG. 4A). Similar percent utilization of glucose (nearly complete) is observed in all samples (FIG. 4B). Consumption of xylose was similar for both levels of ammonium sulfate supplementation (86±0.8% and 89±0.9% for 5 and 10 g/L respectively), but when hydrolysate is supplemented with yeast extract, xylose consumption is only 77±0.8% which may have contributed to the lower titer.

To test the limits of production, improvement of titer is achieved (711±19 mg/L) by adding SD medium and additional glucose, indicating that there is further room for media optimization. The yield is higher at 9.34 $mg_{prespatane}/g_{glucose}$ potentially due to better utilization of glucose over xylose (Bicho et al. 1988; Lee 1992; Wedlock et al. 1989; Dashtban et al. 2015). Even though control medium starts with the highest glucose concentration (105.8 g/L) and has 100% glucose utilization, the titer achieved in control medium (278±20 mg/L) is similar to that of the hydrolysate supplemented with ammonium sulfate while the yield obtained using the control media (2.63 $mg_{prespatane}/g_{glucose}$) is the lowest observed. This indicates that other carbon sources or constituents such as metals, vitamins, or amino acids in the hydrolysate could be utilized for epi-isozizaene production (Yaegashi et al. 2017; Sundstrom et al. 2018) and thus demonstrates the potential of using lignocellulosic biomass for bioconversion processes with *R. toruloides*.

Figure 12A:
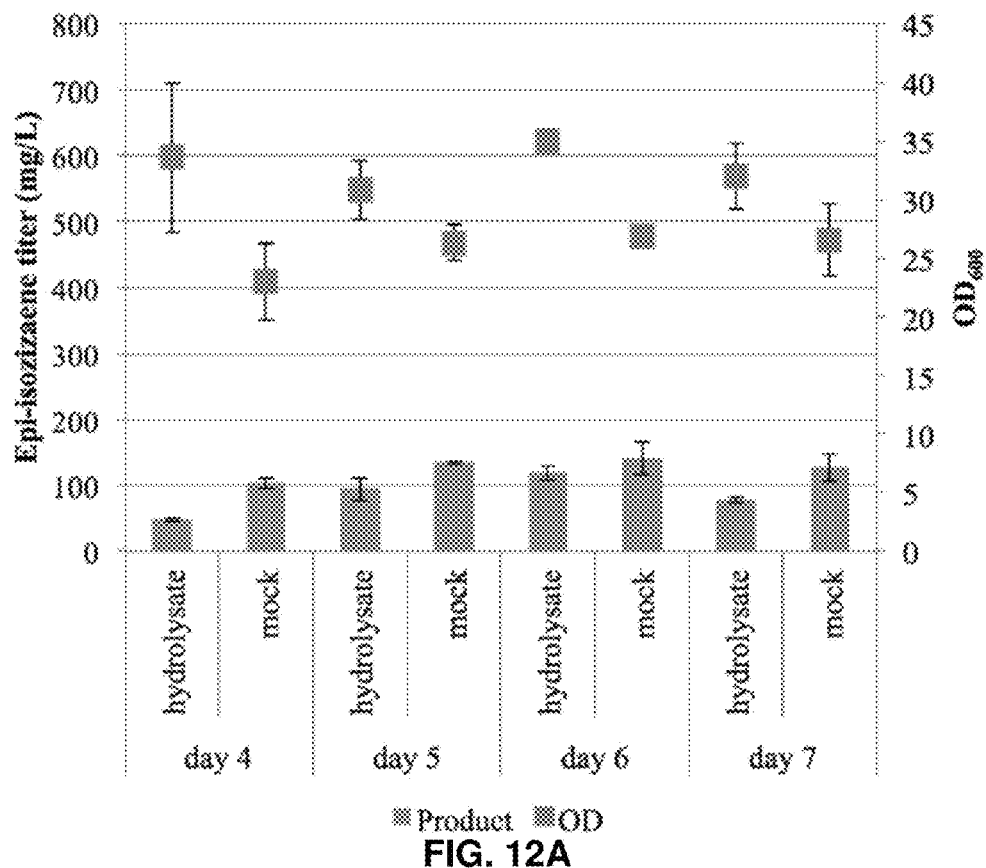
FIG. 12A. Comparison between hydrolysate and mock hydrolysate. Sesquiterpene titer and $OD_{600}$ of strain EIZS2 in filtered batch 2 poplar hydrolysate supplemented with ammonium sulfate 5 g/L and a mock hydrolysate with equivalent sugar. (n=3, data shown as average±standard deviation, from a single experiment).
Figure 12B:
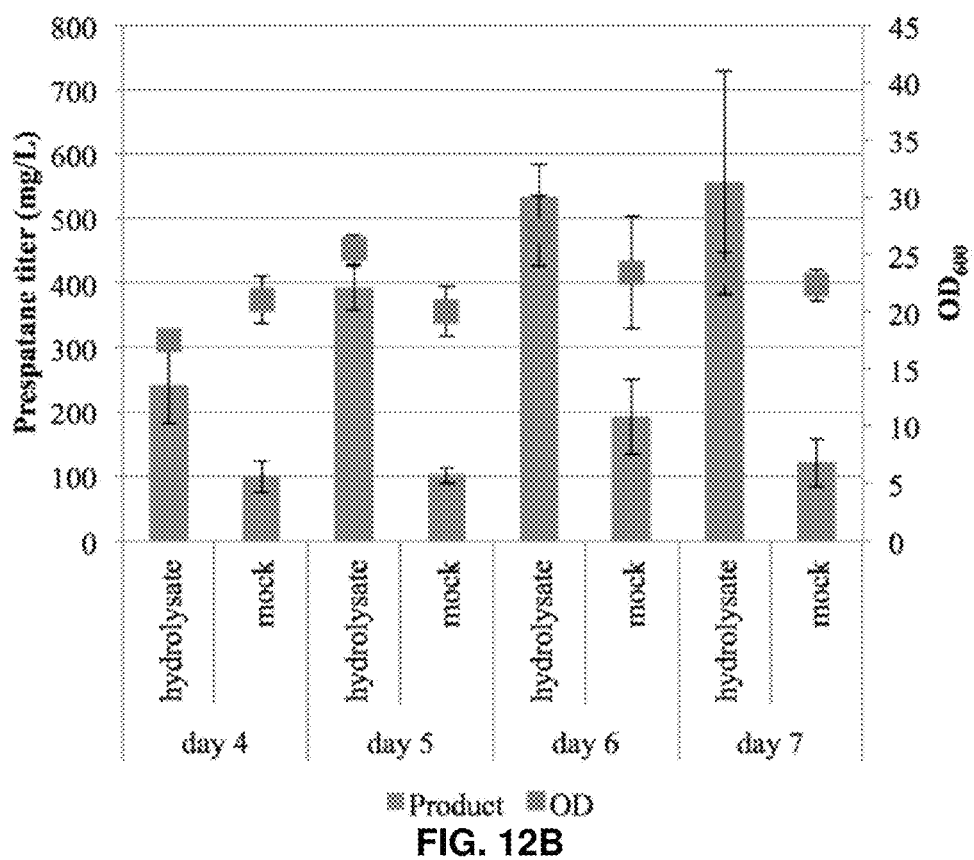
FIG. 12B. Comparison between hydrolysate and mock hydrolysate. Sesquiterpene titer and $OD_{600}$ of strain PPS5 in filtered batch 2 poplar hydrolysate supplemented with ammonium sulfate 5 g/L and a mock hydrolysate with equivalent sugar. (n=3, data shown as average±standard deviation, from a single experiment).
Figures 12C, 13:
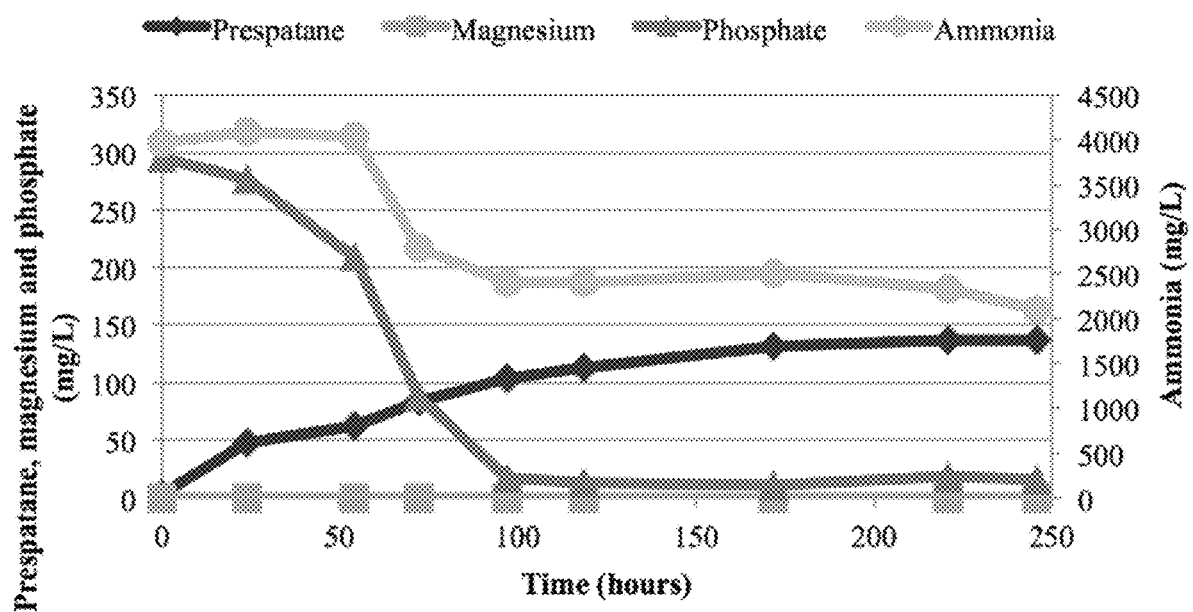
FIG. 12C. Comparison between hydrolysate and mock hydrolysate. Percent utilization of sugar. Time points are taken daily between days 4 and 7. (n=3, data shown as average±standard deviation, from a single experiment).
FIG. 13. Initial 2 L fermentation run which result in low titer, attributed to magnesium and phosphate deficiency, so it is re-run with supplementation. Magnesium, phosphate, ammonia, and prespatane titer of PPS5 with batch 2 hydrolysate.

The optimized media composition is used to better characterize the production of the jet fuel candidates epi-isozizaene and prespatane using the identified high producing clones EIZS2 and PPS5 in filtered batch 2 poplar hydrolysate supplemented with the optimal nitrogen source, ammonium sulfate 5 g/L and compares to production from a mock medium with equivalent glucose and xylose starting concentrations. Samples are taken daily, between day 4 and 7. Cultures grown in mock media reach lower optical densities (600 nm) as compared to the optimized hydrolysate, with mock between 23.01-26.86 and hydrolysate 30.82-34.96 (FIG. 12A). Furthermore, higher titers are obtained from cultures grown in hydrolysate. After a week, titers of PPS5 grown in mock medium (126.3±19.7 mg/L) outperform titers of supplemented hydrolysate (77.8±4.5 mg/L). Glucose utilization is almost identical between hydrolysate (99.24±0.05%) and mock (99.86±0.25%). However, mock medium nearly completes xylose utilization (96.85±0.07%) while hydrolysate does not (28.84±6.33%) (FIG. 12C). PPS5 produces almost five times more prespatane in hydrolysate supplemented with ammonium sulfate 5 g/L (555.7±173.9 mg/L) than in mock medium (120.5±37.5 mg/L) with equivalent glucose and xylose starting concentrations (FIG. 12B). Glucose utilization of hydrolysate is almost complete (97.73±0.04%), matching that of mock. However, xylose utilization is significantly less in hydrolysate (15.93±0.96%) compared to that of mock (96.85±0.07%) (FIG. 12C).

These observations are in agreement with previous studies, describing that heterologous isoprenoid production in hydrolysate is higher as compared to mock hydrolysate (Sundstrom et al. 2018). This indicates the availability of additional, not yet determined carbon sources, metals, vitamins, or amino acids present in the hydrolysate and not accounted for in the mock. The prespatane strain PPS5 is chosen to investigate poplar hydrolysate with 2 L fermentation because it consistently produces higher titer than the epi-isozizaene strain.

Fermentation: Prespatane Production from Poplar in a One-Pot Process Using *Rhodosporidium toruloides*

Previous literature reported better performance of *R. toruloides* (engineered to produce bisabolene and amorphadiene) in corn stover hydrolysate than in defined medium (Yaegashi et al. 2017). One-pot process achieves low cost and high efficiency lignocellulose deconstruction, which is critical for widespread adoption of lignocellulosic biofuels (Sundstrom et al. 2018). To investigate the potential of one-pot poplar hydrolysate as a bioconversion feedstock, key parameters are identified to ensure optimal fermentation of *R. toruloides* engineered to produce the jet fuel candidate prespatane.

An ideal one-pot process would utilize hydrolyzed biomass directly in the fermentation process, with no filtration step included. However, during the generation of hydrolysate, we observe particles that could interfere with fermentation. Therefore, three different configurations are chosen to determine the impact of the biomass particles. Filtered, unfiltered and mock poplar hydrolysates from batch 3 are used in separate fermenters. Mock hydrolysate has equivalent starting glucose and xylose concentrations. The hydrolysates are supplemented with magnesium sulfate 0.5 g/L and potassium phosphate 1 g/L to avoid deficiency witnessed from the first campaign (FIG. 13), where low titers are observed. The poor performance of this first campaign is attributed to magnesium and phosphate deficiency; magnesium is an important cofactor for many enzymatic reactions, and the near-complete consumption of phosphate indicates it is process limiting. Therefore, the campaign is re-run with this supplementation.

High titer is observed when strain PPS5 is fermented in filtered hydrolysate (FIGS. 5A and 5D), reaching prespatane titers of 1.17 g/L and yield 16.6 $mg_{prespatane}/g_{glucose}$ (FIG. 5D) after six days. While both glucose and xylose have been almost completely utilized after 24 hours, titer continues to increase. $OD_{600}$ consistently increases, reaching 188 on day five.

Figure 5B:
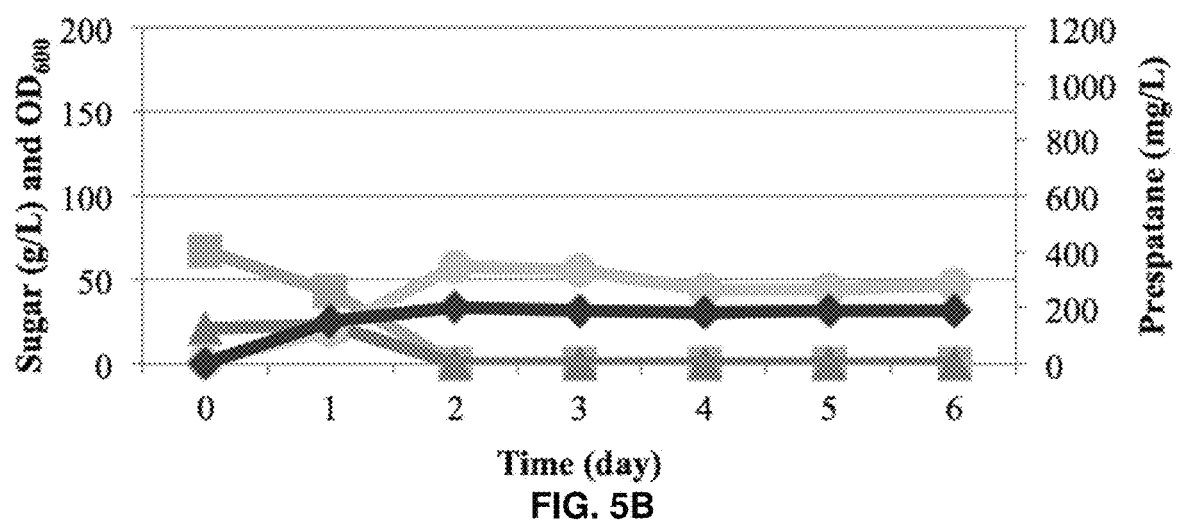
FIG. 5B. Fermentation results. Sugar concentrations, $OD_{600}$, and prespatane titer of bioreactor runs with PPS5 in mock hydrolysate from batch 3.

To determine the impact of biomass and derived compounds in hydrolysate, mock hydrolysate is used in a separate fermenter. Similar to the previous experiment, titer achieved in mock hydrolysate remains below titers obtained in the one-pot process, 189.36 mg/L (FIG. 5B). Titer reaches 200.2 mg/L on day two and slowly begins to decrease, similar with OD. Both glucose and xylose are completely utilized by day two.

Figure 5C:
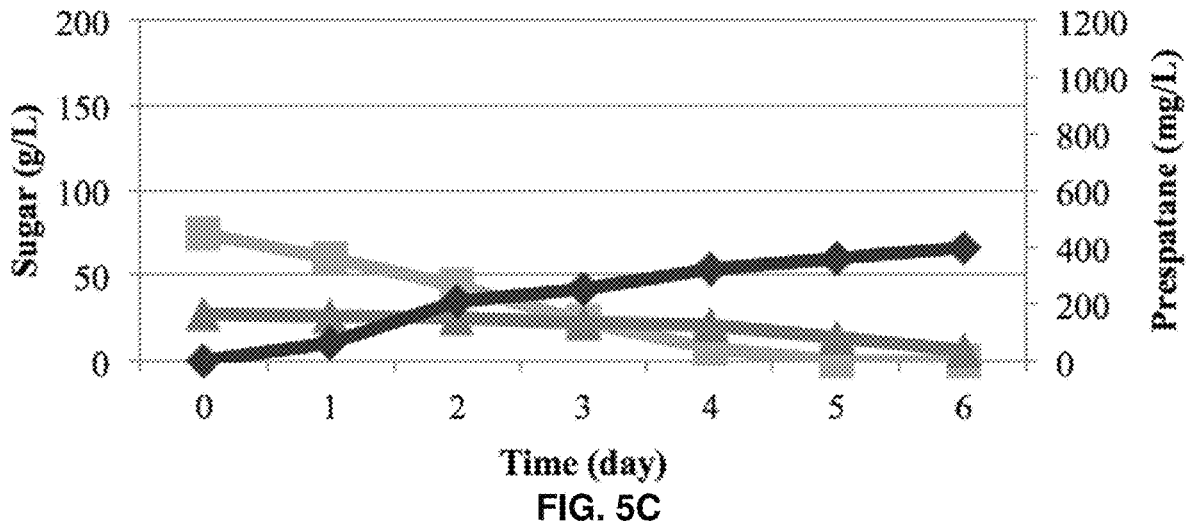
FIG. 5C. Fermentation results. Sugar concentrations, $OD_{600}$, and prespatane titer of bioreactor runs with PPS5 in unfiltered hydrolysate from batch 3.
Figures 5D, 6:
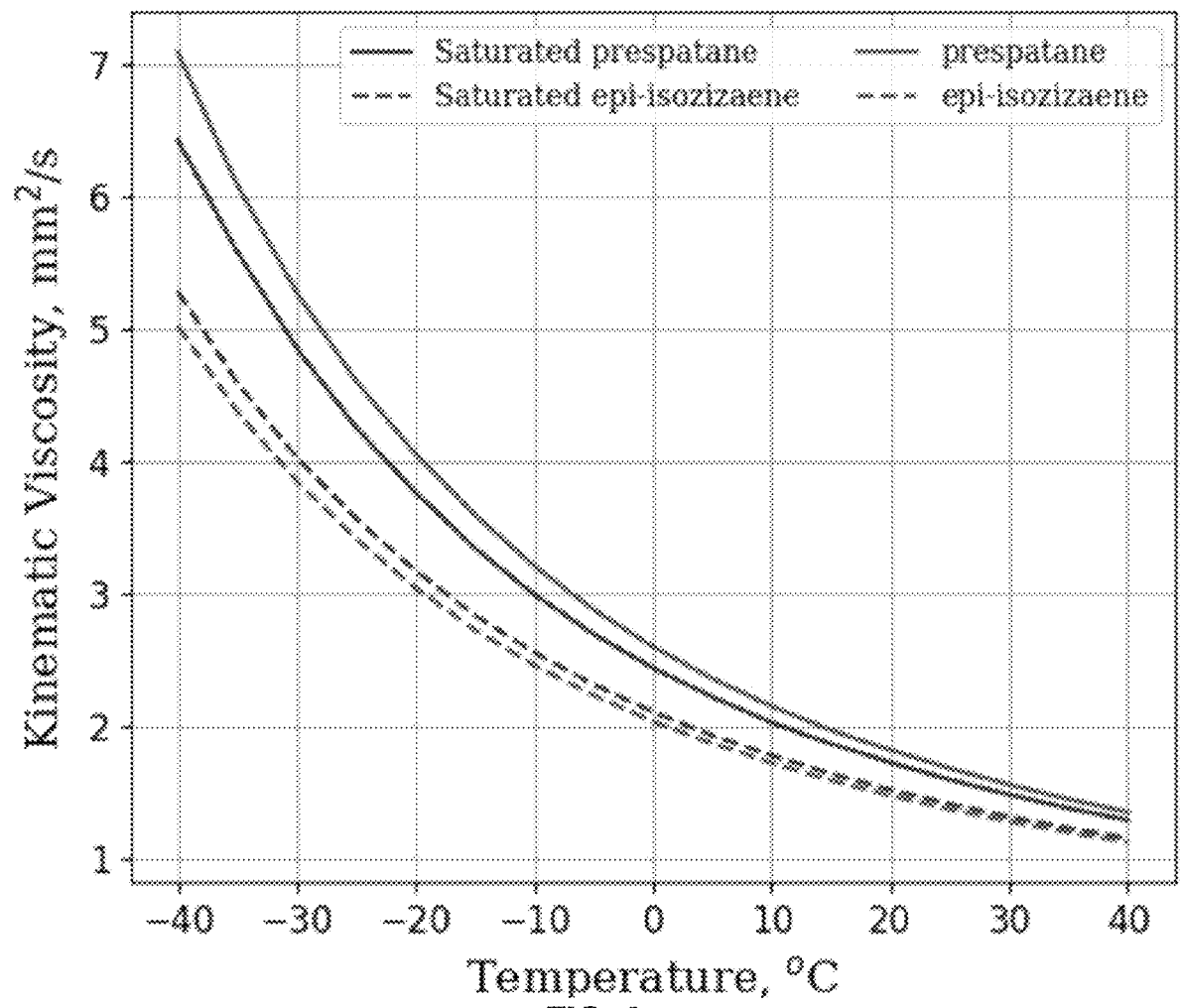
FIG. 5D. Fermentation results. Yield per gram of sugar.
FIG. 6. Viscosities of prespatane, epi-isozizaene, saturated prespatane, and saturated epi-isozizaene, in the temperature range of −40 to 40° C.
Figure 14B:
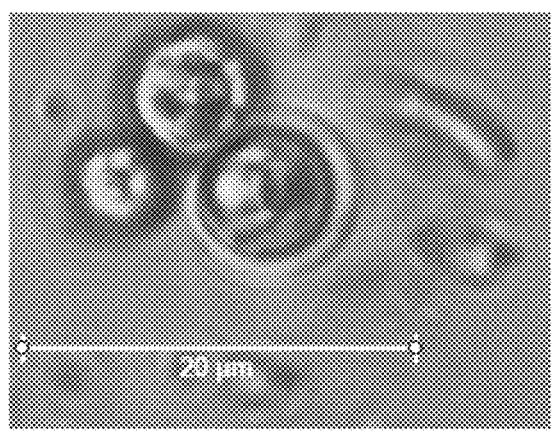
FIG. 14B. Fermentation results of PPS5 from unfiltered hydrolysate batch 3. Microscopy.

Despite the aforementioned particles observed in the unfiltered hydrolysate, strain PPS5 fermented in this media still manages to produce nearly double the titer observed in the mock hydrolysate, reaching 358.22 mg/L after six days (FIG. 5C). However, lower sugar utilization rate is observed in unfiltered hydrolysate; the point at which glucose has been completely utilized occurs much later, and 14.05 g/L of xylose remains. To determine if visual cues can enlighten the cause of this, microscopy is performed on day 5 for cells in filtered (FIG. 14C) and unfiltered hydrolysate (FIG. 14B). In the unfiltered hydrolysate, a spike in lactic acid suggests potential bacterial contamination which soon is consumed (FIG. 14A). *R. toruloides* has been shown to have the ability to consume lactic acid (Sundstrom et al. 2018). Additionally, *R. toruloides* cells exhibit distressed morphological phenotypes in the unfiltered hydrolysate, appearing significantly larger and more spherical. This may be due to continuous particle bombardment of the cells by the clearly visible biomass particles. This phenomenon is not observed in previous one-pot fermentations utilizing sorghum hydrolysate, indicating that this is a unique phenomenon caused by poplar hydrolysate, and warrants further investigation.

Prespatane titers are shown to be improved when transitioning from mock hydrolysate to either filtered or unfiltered one-pot poplar hydrolysate. A maximum prespatane titer of 1.17 g/L is observed, representing almost 10% of the maximum biochemical yield. Engineering to increase terpene precursor levels is expected to further enhance this yield. Together, these results demonstrate the potential of using one-pot hydrolysate in bioconversion similar to (Sundstrom et al. 2018).

CONCLUSION

In conclusion, incorporating the tricyclic sesquiterpenes epi-isozizaene and prespatane produced heterologously from *R. toruloides* with one-pot poplar hydrolysate, holds great promise for the expansion of renewable bioderived jet fuel. This represents the necessary innovation required to establish a sustainable jet fuel blend from bioconversion of lignocellulosic feedstock. As a result of sesquiterpenes having a high cetane number and energy density, making them an attractive next-generation jet fuel alternative, two tricyclic sesquiterpenes, epi-isozizaene and prespatane as well as their hydrogenated states are examined to evaluate their alternative-fuel viability. Various theoretical fuel properties, including energy density and specific energy, are compared to Jet A and farnesene, an alternative jet fuel. Prespatane is identified as a novel alternative jet fuel blend and demonstrate sustainable heterologous production along with epi-isozizaene, using the oleaginous yeast R. toruloides.

To improve the sustainability of biofuel production, hydrolysate from lignocellulosic biomass has been incorporated as a bioconversion resource. Specifically, R. toruloides is demonstrated to be able to convert one-pot poplar lignocellulosic hydrolysate, to epi-isozizaene and prespatane. Furthermore, scalability is demonstrated when the optimal hydrolysate process with nitrogen supplementation proves robust with improved performance from bench to large scale, reaching 1.17 g/L prespatane in a 2 L bioreactor. Prespatane titers improve when transitioning from mock and unfiltered hydrolysate to filtered IL hydrolysate and full consumption of all measured carbon sources is observed within 48 hours of fermentation, demonstrating the promise of R. toruloides as production host for efficient conversion of IL pretreated biomass. This is the first demonstration of a fully consolidated process combining optimization of IL pretreatment and enzymatic saccharification of poplar feedstock. With further intensification and optimization, this process presents a promising new approach towards commercial production of lignocellulosic jet fuel blends.

Materials and Methods
Theory Prediction Methodology

For Table 1, boiling point predictions are made by using the Stein and Brown method (Stein and Brown 1994), which is a variant of the more widely known Joback and Reid method (Joback and Reid 1987). In the Stein and Brown method the Joback and Reid result is augmented using the following equation:

$$T_b(corr) = T_b - 94.84 + 0.5577 T_b - 0.0007705 T_b^2,$$

where $T_b$ is the Joback Reid result, and $T_b(corr)$ is the Stein and Brown result. The method, using a dataset of 6584 compounds, has an average absolute error of 20.4 K, and an average percent error of 4.3%. Equation of State (EoS) modeling requires several basic inputs, one of which is the ideal heat capacity ($Cp_{,ideal}$). The DIPPR (Design Institute for Physical Properties) database is a repository which contains these inputs for a large array of molecules however, when these inputs are not available, estimates of them can be obtained. $Cp_{,ideal}$ is obtained by calculating the optimal geometry of the target molecule, and performing a subsequent frequency analysis. The frequency analysis acts as inputs to established statistical thermodynamics equations, which relate frequencies to $Cp_{,ideal}$. The program thermo.pl is used to convert frequencies to $Cp_{,ideal}$ (Irikura 2002). The geometry optimization/frequency calculation is performed using the B3LYP/6-311G** method (Becke 1993; Lee et al. 1988), and $Cp_{,ideal}$ is calculated from 0 to 1000 K. The resulting $CP_{,ideal}$ values are then fitted to a $4^{th}$-order polynomial, and used as an input to the Multiflash thermodynamic modeling program (Process Systems Enterprise 1997). Also as input, the critical thermodynamic values ($T_c$, $P_c$) are required. They are obtained by using the group contribution method as outlined by Marrero et. al (Marrero and Gani 2001). The standard deviations are 6.99 K, and 1.39 bar, respectively, and so yields accurate estimates of $T_c$ and $P_c$. Liquid viscosity is calculated by using both the SuperTRAPP, and the Pederson equation. These are two corresponding states methods, which yield accurate viscosities for both pure and complex mixtures, applicable to the oil and gas industry (Pedersen et al. 1984). A description of the SUPERTRAPP method, and the full Pederson equation is listed below. The SUPERTRAPP viscosity model is an extended corresponding states method. It uses a combination of the viscosity of a reference fluid (in this case propane), its critical thermodynamics properties, and those of the pure/mixture fluid in order to obtain accurate viscosity estimates. The SUPERTRAPP method can be described by the following equation:

$$\eta(T, \rho) = \eta_{ref}(T/g, \rho h)\left[\frac{M^{\frac{1}{2}}}{M_{ref}^{\frac{1}{2}}}\right] g^{\frac{1}{2}} h^{\frac{-2}{3}} X_\eta,$$

where $X\eta$ is a correction factor for noncorrespondence, M is the molar mass, $\eta$ is the viscosity, and the subscript, ref, refers to the reference fluid. g and h are variables dependent on the critical thermodynamic properties, and can be calculated using the equation from Ely and Hanley (Ely and Hanley 1981). The pedersen equation is listed below:

$$\eta_L(P, T) = \left(\frac{T_C^{-\frac{1}{6}}}{T_{cr}^{-\frac{1}{6}}}\right)\left(\frac{P_C^{\frac{2}{3}}}{P_{cr}^{\frac{2}{3}}}\right)\left(\frac{MW^{\frac{1}{2}}}{MW_r^{\frac{1}{2}}}\right)\left(\frac{\alpha}{\alpha_r}\right)\eta_r(P_r, T_r),$$

where $T_c$ is the critical temperature in Kelvin, $P_c$ is the critical pressure in bar, MW is the molecular weight, $\eta$ is the viscosity, and the subscript 'r' refers to the reference fluid.

$$\alpha = 1.000 \pm 7.387 x^{-3} Q_T^{1.847} MW^{0.5173}$$

$$\alpha_r = 1.000 + 0.031 Q_r^{1.847},$$

where $Q_r$ is the reduced density of the reference fluid, in this case methane. These models are not dependent on an EoS, but rather are dependent on the critical thermodynamic properties of the target molecule/mixture, and the reference fluid.

Additionally, a blend model for a conventional jet fuel is developed. The jet fuel modeled is an A-2 POSF 10325 Jet A fuel. The blend model is developed by utilizing a published GCxGC analysis, and incorporating those chemical species which make more than 1 vol % contribution to the fuel (Edwards 2017). Due to limitations in the GCxGC analysis, only the general type of molecule and the extent to which it is present are known. Therefore, some reasonable assumption as to the type of molecules present need to be made. For example, all alkylbenzenes are assumed to be n-alkylbenzenes. Di-aromatics are fully represented by naphthalene. Cycloaromatics are modeled as alkyltetralins. Isoparaffins are modeled as 2-methylalkanes. Monocycloparaffins are modeled as n-alkylcyclohexanes, and dicycloparaffins are represented by cis-decalin. Tricycloparaffins, making only trace contributions, are excluded. Viscosity curves of the modeled Jet A fuel, as a function of temperature, are calculated using both the SUPERTRAPP and Pedersen method, and compared to experimental data. Viscosity curves of saturated prespatane and isozizaene, blended into this blend model are calculated using the SUPERTRAPP method.

Energy density and Specific energy calculations are performed using ab-initio calculations. Initially, a geometry optimization of the target molecule is performed using the B3LYP/6-311G** method. Frequencies are calculated at the same level of theory. All real, positive valued, frequencies are evidence that the optimized geometry is a minima on the Potential Energy Surface (PES). Once an optimized geometry is obtained, a single point ab-initio calculation is performed using the CBS-QB3 (Complete Basis Set) method. In a CBS method, more accurate energetics are obtained by performing a series of single point energy calculations. The resulting energies of these calculations are used as inputs in extrapolative equations. In a test of several hundred molecules in the G2/97 test set, the maximum average deviation in energy of the CBS-QB3 method is 3.63 KJ/mole (Montgomery et al. 2000). In order to calculate the Heat of Combustion (HOC) of a target molecule, the CBS-QB3 method was run for $O_2$, $CO_2$, $H_2O$, and the target molecule. From the CBS-QB3 method, the Heat of Combustion (HOC) is obtained by noting the balanced chemical equation for combustion, and utilizing the following equation:

$$HOC = \left(\sum_{prod} H^\circ - \sum_{react} H^\circ\right) + HOV,$$

where HOV is the enthalpy of vaporization. Once the HOC is known, the Specific energy and the Energy density can be obtained by using the molecular weight, and the liquid density, respectively. All ab-initio calculations are run using the Gaussian 09 computational suite (Frisch et al. 2016). EoS calculations are carried out using the Multiflash program (Process Systems Enterprise 1997).

Plasmid Design and Construction

Figure 1B:
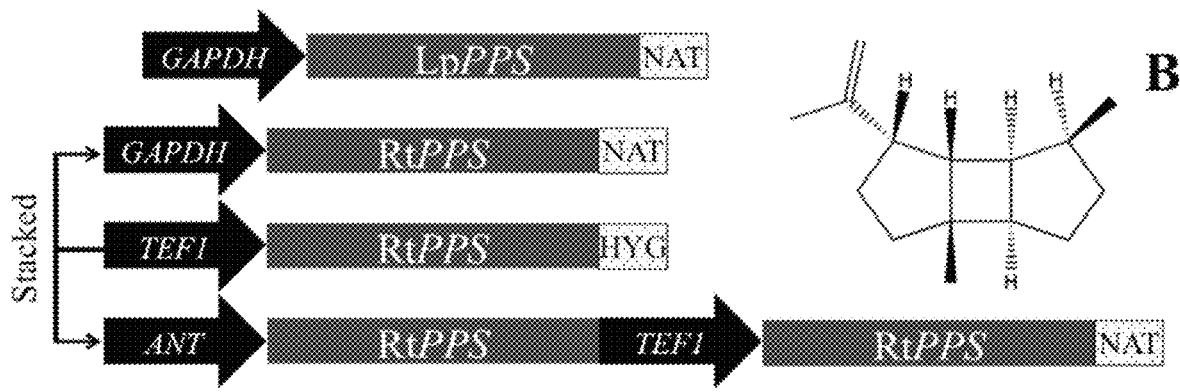
FIG. 1B. Constructs of relevant plasmids as well as their product chemical structures: prespatane. Arrows labeled "stacked" represent TEF1-HYG constructs used to transform onto highest perspective sesquiterpene producing strains with NAT resistance to increase gene copy number. Rt represents R. toruloides codon optimized genes while Sc and Lp represent native genes from S. coelicolor and L. pacifica.

Plasmids and strains used in this study can be found in Table 2, and are also available through Joint BioEnergy Institute Strain Registry (webpage for: public-registry.jbei, org) (Ham et al. 2012)) and are available upon request. Codon optimization, gene synthesis, and plasmid construction is performed by Genscript (Piscataway, N.J.). Overall, two sets of four plasmids are designed and tested for the expression of two heterologous enzymes to produce jet fuel: the epi-isozizaene synthase (EIZS) from *Streptomyces coelicolor* A3(2) (NCBI accession number, WP 011030119.1) and the prespatane synthase (PPS) from *Laurencia pacifica* (ASV63464.1). An overview of the plasmids used in this study is shown in FIG. 1. Of those constructs, one contains the native enzyme sequence (ScEIZS and LpPPS, respectively) while the other three contain sequences codon optimized for expression in *R. toruloides* (RtEIZS and RtP P S) Codon optimization is based on a custom IFO0880 codon usage table (webpage for: genomejgi.doe.gov/Rhoto_IFO0880_3/Rhoto_IFO0880_3.home.html). The promoters GAPDH, TEF1 and ANT are used to drive the expression of the heterologous gene. One design has two gene copies, driven by both ANT and TEF1, respectively. Constructs are synthesized and inserted into the *Agrobacterium tumefaciens* mediated transformation (ATMT) plasmid pGI2 (Abbott et al. 2013) using the EcoRV restriction sites. The pGI2-derived plasmids are introduced into *R. toruloides* recipient strains by ATMT as previously described (Zhang et al. 2016; Zhuang et al. 2019).

Table 2. Relevant plasmids, genotypes/features, source/references, JBEI registry ID's and strains. GAPDH, glyceraldehyde 3-phosphate dehydrogenase; TEF1, translational elongation factor; ANT, adenine nucleotide translocase; ScEIZS, epi-isozizaene synthase from *Streptomyces coelicolor* A3(2) (NCBI accession number, WP 011030119.1); RtEIZS, epi-isozizaene synthase from *S. coelicolor* A3(2) codon optimized for *R. toruloides*; LpPPS, prespatane synthase from *Laurencia pacifica* (ASV63464.1); RtPPS, prespatane synthase from *L. pacifica* codon optimized for *R. toruloides*; $NAT^R$, nourseothricin resistance; $HYG^R$, hygromycin B resistance.

|  | Genotypes/features | Source/references | JBEI registry ID |
|---|---|---|---|
| Plasmids | | | |
| construct 1 | $P_{GAPDH}$-ScEIZS-$NAT^R$ | This study | JPUB_013517 |
| construct 2 | $P_{GAPDH}$-RtEIZS-$NAT^R$ | This study | JPUB_013519 |
| construct 3 | $P_{TEF1}$-RtEIZS-$HYG^R$ | This study | JPUB_013521 |
| construct 4 | $P_{ANT}$-RtEIZS-$P_{TEF1}$-RtEIZS-$NAT^R$ | This study | JPUB_013523 |
| construct 5 | $P_{GADPH}$-LpPPS-$NAT^R$ | This stady | JPUB_013525 |
| construct 6 | $P_{GADPH}$-RtPPS-$NAT^R$ | This study | JPUB_013527 |
| construct 7 | $P_{TEF1}$-RtPPS-$HYG^R$ | This standy | JPUB_013529 |
| construct 8 | $P_{ANT}$-RtPPS-$P_{TEF1}$-RtPPS-$NAT^R$ | This study | JPUB_013531 |
| Strains | | | |
| IFO0880 (WT) | *Rhodospordium toruloides* strain IFO0880, mating type A2 | NBRC culture collection | |
| EIZS 1 | IFO0880/$P_{TEF1}$-RtEIZS-$HYG^R$ | This study | JPUB_013534 |
| BIZS 2 | IFO0880/$P_{GAPDH}$-RtEIZS-$NAT^R$ | This stady | JPUB_013532 |
| EIZS 3 | IFO0880/$P_{GAPDH}$-RtEIZS-$NAT^R$/ $P_{TEF1}$-RtEIZS-$HYG^R$ | This study | JPUB_013533 |
| BIZS 4 | IFO0880/$P_{ANT}$-RtEIZS-$P_{TEF1}$-RtEIZS-$NAT^R$ | This study | JPUB_013535 |
| EIZS 3 | IFO0880/$P_{ANT}$-RtEIZS-$P_{TEF1}$-RtEIZS-$NAT^R$/ $P_{TEF1}$-RtEIZS-$HYG^R$ | This study | JPUB_013536 |
| PPS 1 | IFO0880/$P_{TEF1}$-RtPPS-$HYG^R$ | This study | JPUB_013539 |
| PPS 2 | IFO0880/$P_{GAPDH}$-RtPPS-$NAT^R$ | This study | JPUB_013537 |
| PPS 3 | IPO0880/$P_{GAPDH}$-RtPPS-$NAT^R$/ $P_{TEF1}$-RtPPS-$HYG^R$ | This study | JPUB_013538 |
| PPS 4 | IFO0880/$P_{ANT}$-RtPPS-$P_{TEF1}$-RtPPS-$NAT^R$ | This stady | JPUB_013540 |
| PPS 5 | IFO0880/$P_{ANT}$-RtPPS-$P_{TEF1}$-RtPPS-$NAT^R$/ $P_{TEF1}$-RtPPS-$HYG^R$ | This study | JPUB_013541 |

Transformation and Screening of *R. toruloides*

ATMT with strain EHA 105 is performed using *R. toruloides* IFO0880, previously described (Zhang et al. 2016). Twenty random transformants of each construct are randomly selected and cultivated in 0.5 mL Difco YPD (yeast extract 10 g/L, peptone 20 g/L, and glucose 20 g/L) (VWR, 90003-284, Radnor, Pa.) in a 96-well plate (Corning, 3960, Corning, N.Y.) with gas-permeable sealing film (m2p-labs, F-GP, Baesweiler, Germany) for 24 hours, shaking on a Multitron (INFORS HT, 110003, Bottmingen, Switzerland)

at 31° C., 1,000 rpm and 70% humidity. The following day, 50 µl of the saturated culture is transferred into 950 µl YPD in a 48-well flower plate (m2p-labs, M2P-48-B). 20% dodecane overlay with spiked with an internal standard (200 mg/L pentadecane) is added to the production cultures (Sigma-Aldrich, 76510, St. Louis, Mo.). After 7 days of cultivation, at 30° C., 1,000 rpm, with 70% humidity in the Multitron shaker, the production cultures are centrifuged (21,130×g, 5 minutes) to separate the overlay from the cultivation media. Centrifugation is in an Eppendorf 5424 Microcentrifuge (Eppendorf AG, 022620428, Hamburg, Germany).

Quantification of Sesquiterpenes

The highest producing clone of each construct is identified (FIGS. 10 and 11A to 11F). The plasmid containing the HYG selection marker is transformed onto the respective highest producing clone with NAT resistance (e.i. stacking). The highest producing stacked strains are identified and grown in parallel with the original parent strain to confirm titer differences (FIGS. 2A and 2B). Ethyl acetate or dodecane are used to make dilutions (1:10, 1:50, 1:100, 1:125, 1:200, and 1:250) of the overlay with a total volume of 200 µL or 600 µL. The internal standard pentadecane (250 mg/L) is used in the overlay at the beginning of the experiment. Caryophyllene (40 mg/L) and ent-kaurene (40 mg/L) are used as internal standards during dilution. Titer is determined using a conversion factor with pure bisabolene standards. The conversion factors are calculated by comparing SIM and SCAN corrected peak area of bisabolene to that of epi-isozizaene and prespatane. Overlay is analyzed with gas chromatography-mass spectrometry (GC-MS) using an Agilent 69890 Plus gas chromatograph (Agilent Technologies, G1530A, Santa Clara, Calif.) operating with an Agilent 5973 Network mass spectrometer (Agilent Technologies, G1099A). 1 µL of each sample is injected by a CombiPal autosampler (CTC Analytics, MXY 02-00B, Zwingen, Switzerland). Analytes are separated on a DB-5MS column (30 m long, 0.25 mm internal diameter, 0.25 µm film thickness, Agilent Technologies, 122-5532) using the following oven parameters: hold for 0.75 min at an initial temperature 100° C., followed by a temperature ramp of 40° C./min to 300° C. The mass spectrometer was operated in selected ion mode, with target ions (m/z) of 71, 85, 119, 161, 189 and 204. Analysis was performed on Enhanced ChemStation (Agilent Technologies, MSD Chemstation E.02.00.493).

One-Pot Poplar Pretreatment and Saccharification

Figure 3:
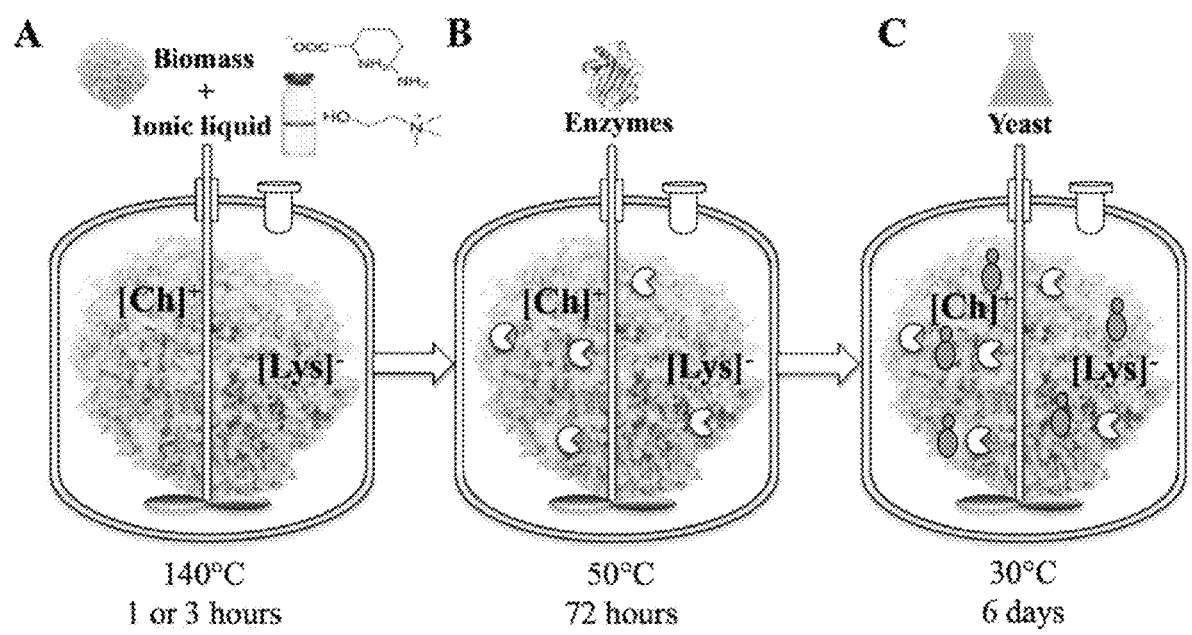
FIG. 3. The one-pot pretreatment process making milled poplar into hydrolysate. (A) Thirty or twenty-five percent biomass loading is achieved with ten percent ionic liquid cholinium lysinate ([Ch]$^+$ [Lys]$^-$) in reactor. Once mixed thoroughly, the reactor is closed, heated to 140° C., and stirred for one or three hours. (B) Sulfuric acid at 50% (v/v) is added. pH may be adjusted to 4.8-5, if necessary. The enzymes CTec3:HTec3 (or CTec2:HTec2) are added at ratio of 9:1 (v/v) per gram of untreated biomass. Reactor is heated to 50° C. and stirred for 72 hours. (C) Yeast is added and grown at 30° C. for six days. If necessary, the hydrolysate can be filtered beforehand.

One-pot process is performed as described by Sundstrom et al. with minor modifications (FIG. 3 and Table 3) (Sundstrom et al. 2018). Poplar, with the biomass composition of glucan 42.6 wt % and xylan 15.6 wt % is used as feedstock. The ionic liquid pretreatment and enzymatic hydrolysis are conducted in an automated 1 L Parr reactor system (Parr Instrument Company, Moline, Ill., USA). 30% biomass loading is achieved by using 30 g of biomass in 10:90 [Ch][Lys]: water. The pretreatment is carried out at 140° C. for 1 hour with stirring at 90 rpm powered by a 4875 process controller using three-arm, self centering anchor with PTFE wiper blades. After pretreatment, the pH is adjusted to 5 by adding 1.3 ml $H_2SO_4$ at 50% v/v (i.e 0.3 mol) and the IL-treated biomass is diluted to achieve a solids loading of 20% w/w. The accessibility of enzymes to cellulose and hemicellulose in the poplar is quantified by the yield of sugars (glucose and xylose) released during enzymatic hydrolysis. The cellulase and hemicellulose Cellic® complex CTec3/HTec3 (9:1) are used at loading of 30 mg protein/g of biomass. The reaction is carried out for 72 hours at 50° C. and 90 rpm agitation. The supernatant is analyzed by HPLC for monosaccharide detection *Sundstrom et al. 2018). Enzymatic digestibility is defined as the glucose yield based on the maximum potential glucose from glucan in biomass. In the calculation of cellulose conversion to glucose, it is considered cellulose: glucose ratio of 1:1.11 (Li et al. 2010). Overall, three individual batches of poplar hydrolysate are prepared with minor modifications (Table 3).

TABLE 3

Comparison of pretreatment, enzymatic saccharification, and sugar generation between poplar hydrolysate batches and sorghum method referenced (Sundstrom et al. 2018). The highlighted step variation is between biomass loading, pretreatment duration, and enzymes.

|  | Batch 1 | Batch 2 | Batch 3 | Sundstrom et al., 2018 |
|---|---|---|---|---|
| Pretreatment | | | | |
| Biomass loading, % | 30 | 25 | 25 | 30 |
| [Ch][Lys]:water | 1:9 | 1:9 | 1:9 | 1:9 |
| Temperature, ° C. | 140 | 140 | 140 | 140 |
| Duration, hour | 1 | 3 | 3 | 1 |
| Enzymatic saccharification | | | | |
| $H_2SO_4$ pH adjustment to 5, v/v | 50 | 50 | 50 | 50 |
| Solids loading, w/w | 20 | 20 | 20 | 20 |
| Cellic enzymes | CTec3/HTec3 | CTec2/HTec2 | CTec3/HTec3 | CTec2/HTec2 |
| Enzyme : water | 9:1 | 9:1 | 9:1 | 9:1 |
| Temperature, ° C. | 50 | 50 | 50 | 50 |
| Duration, hour | 72 | 72 | 72 | 72 |
| Sugar, g/L | | | | |
| Glucose | 46.3 | 50 | 77 | — |
| Xylose | 14.2 | 16.5 | 26.6 | — |

Bench-Scale Nitrogen Source Optimization: Conversion of Poplar Hydrolysate into Jet Fuel Candidates Batch 1 poplar hydrolysate is filtered (0.2 VWR, 97066-212) and supplemented with various nitrogen sources, summarized in FIGS. 4A and 4B. Those include ammonium sulfate 5 g/L and 10 g/L, yeast extract 10 g/L, and ammonium sulfate 5 g/L with Synthetic Defined medium (SD) and glucose 40 g/L. pH was adjusted to 7.5. Synthetic Defined (SD) medium had Difco™ Yeast Nitrogen Base without amino acids 6.7 g/L (BD, 291940, Franklin Lakes, N.J.), CSM powder 0.79 g/L (Sunrise Science Products, 1001-100, San Diego, Calif.), and is pH adjusted to 7 using 2 M NaOH. The control medium is yeast extract 10 g/L, peptone 20 g/L, and glucose 100 g/L.

Using triplicate test tubes, the highest epi-isozizaene strain, EIZS2 (JPUB_013532), is grown in 5 mL of supplemented hydrolysate. To collect the sesquiterpene throughout the growth experiment, a 20% dodecane overlay is added. Optical density at 600 nm ($OD_{600}$), sugar and sesquiterpene titer in dodecane overlay are collected after seven days growth in a 48-well flower plate (FIGS. 4A and 4B). Samples are diluted 1:10 in HPLC grade water (Honeywell, AH365-4, Charlotte, N.C.) and starting sugars 1:50. Sugars are quantified by HPLC using an Agilent Technologies 1200 series instrument equipped with an Aminex HPX-87H column (BioRad Laboratories, USA) and a refractive index detector, kept at 60° C. and 35° C., respectively, during analysis (FIG. 4B). The mobile phase is 4 mM sulfuric acid with a flow rate of 0.6 mL/min. 5 µL sample injection volumes are used. Prior to analysis, samples are filtered using 0.45 µm nylon centrifuge filters. Concentrations are calculated by comparison of the resulting peak areas to calibration curves made with pure standards.

Determining Fermentation Strain

After 0.2 μm filtration, the hydrolysate from batch 2 is supplemented with the optimal nitrogen source, ammonium sulfate 5 g/L. Using triplicate test tubes, the top strains PPS5 and EIZS2 (JPUB_013541) are grown in 5 mL of the supplemented batch 2 hydrolysate. A mock medium (YPD 50 g/L, glucose 30 g/L, and xylose 16.5 g/L) is used as a control with the same starting concentration of glucose and xylose as the batch 2 hydrolysate. A twenty-percent dodecane overlay is used. $OD_{600}$, sugar and sesquiterpene titer are collected daily between day four and seven (FIGS. 12A to 12C).

Hydrolysate Preparation for Bioreactor Run

Batch 3 poplar hydrolysate is prepared with CTec3 (protein concentration: 107.7±2.1 mg mL$^{-1}$) and hemicellulase HTec3 (protein concentration: 80.4±5.4 mg mL$^{-1}$) complex for enzymatic hydrolysis (Table 3). They are loaded at a fixed ratio based on the initial biomass content (27 mg CTec3/g biomass, 3 mg HTec3/g biomass). After 72 hours of saccharification the poplar hydrolysate is collected for fermentations experiments carried out using unfiltered hydrolysate and filtered hydrolysate (without solids). The filtered batch 3 hydrolysate is collected by filtering through a 0.7 μm glass fiber filter (Whatman, Maidstone, UK) and sterilized via 0.2 μm filtration. The hydrolysate contains concentrations of 77 g/L glucose (90.3% yield), 26.6 g/L xylose (85.5% yield), and 11.9 g/L acetic acid. The composition of the mock hydrolysate is designed to closely match the sugar concentration of poplar hydrolysate. It consists of yeast extract (10 g/L), peptone (20 g/L), glucose (77 g/L) and xylose (26.6 g/L).

Seed Cultures

The highest producing prespatane strain, PPS5, is selected for fermentation (FIGS. 5A to 5D). Cell growth during seed culture is performed in three steps. First, cells are cultured aerobically in 5 mL YPD media. Then, cells are transferred to 50 mL YPD media and 50 mL of liquid media containing 25% (v/v) poplar hydrolysate and 75% (v/v) YPD. After this step, cells grown in 25% hydrolysate are used to inoculate a 50:50 mixture of YPD and hydrolysate. In all steps, inoculum is 10% (v/v) and the cells are incubated at 30° C., 200 rpm for 24 hours.

2 L Bioreactor Fermentations

Batch fermentations are performed in 2 L Sartorius fermenters (Sartorius Stedim, Gottingen, Germany) using batch 3 filtered and unfiltered poplar hydrolysate and a mock hydrolysate. One tank is batched with 900 mL unfiltered hydrolysate, one tank contains 787 mL of filtered hydrolysate (considering 12.6% the solid content of the hydrolysate) and 787 mL of mock hydrolysate is used for another tank. For all experiments, 10% (v/v) inoculum and 20% (v/v) dodecane, containing 1 g/L pentadecane as internal standard, are added aseptically into the fermenters in the beginning of the process. Additionally, all reactors are supplemented with ammonium sulfate, magnesium sulfate and potassium dihydrogen phosphate to a final concentration of 5 g/L, 0.5 g/L and 1 g/L, respectively.

Unfiltered hydrolysate is pasteurized at 80° C. for 1 hour and all the other components are filtered sterilized (0.2 μm pore size filters). To prevent bacterial contamination, 1 mL of 30% (w/v) cefotaxime is added to the batch medium. Fermenters are controlled at 30° C. and initial pH is adjusted to pH 7 and controlled at pH 5 with 2 N NaOH. Dissolved oxygen is cascade-controlled at 20% via agitation (500-1, 200 rpm) and air flow (0.5-1.5 LPM). Samples are taken in regular intervals and centrifuged to separate aqueous and solvent fraction.

Microscopy

Figure 14C:
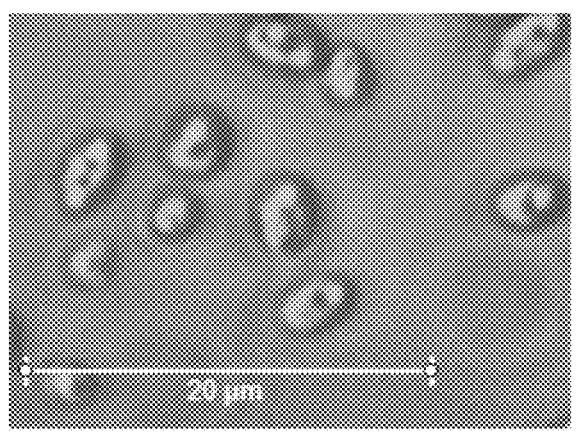
FIG. 14C. Fermentation results of PPS5 from unfiltered hydrolysate batch 3. Microscopy from filtered hydrolysate fermentation.

Cellular morphology is assayed using 2 mL of culture recovered from bioreactors on day 5 of growth (FIGS. 14B and 14C). Cells are diluted 1:100 in water, and 10 μL are used for observation under the microscope. Cells are observed at 63× magnification using a Leica DM6 B microscope (Leica Microsystems, Switzerland) operating with a DM6B-Z Master control panel, version 2.10.15. Images are captured using an ORCA-Flash 4.00LT camera (Hamamatsu, C11440-42CU, Japan) operating on a computer running Lecia Application Suite X (Version 2.0.0.14332), where 20 μm scale bars are added. Images are exported into GNU Image Manipulation Program for enhancing brightness, contrast, and image cropping. This does not affect the relative size of cells to scale bars.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified fungal host cell capable of producing prespatane comprising prespatane synthase (PPS) wherein the PPS comprises an amino acid sequence having at least 70% identity with SEQ ID NO:1.

2. The genetically modified host cell of claim 1, wherein the genetically modified host cell is a yeast.

3. The genetically modified host cell of claim 2, wherein the genetically modified host cell is of the genus *Rhodosporidium*.

4. The genetically modified host cell of claim 3, wherein the genetically modified host cell is *Rhodosporidium toruloides*.

5. The genetically modified host cell of claim 1, wherein the PPS comprises an amino acid sequence having DDXXD (SEQ ID NO:3) or DDXXE (SEQ ID NO:4).

6. The genetically modified host cell of claim 5, wherein the PPS comprises an amino acid sequence having at least 80% identity with SEQ ID NO:1.

7. The genetically modified host cell of claim 6, wherein the PPS comprises an amino acid sequence having at least 90% identity with SEQ ID NO:1.

8. The genetically modified host cell of claim 7, wherein the PPS comprises an amino acid sequence having at least 95% identity with SEQ ID NO:1.

9. The genetically modified host cell of claim 8, wherein the PPS comprises an amino acid sequence having at least 99% identity with SEQ ID NO:1.

10. The genetically modified host cell of claim 9, wherein the PPS comprises SEQ ID NO:1.

11. The genetically modified host cell of claim 1, further comprising one or more enzymes of the mevalonate (MVA) pathway, wherein the MVA pathway is heterologous to the genetically modified host cell.

12. The genetically modified host cell of claim 11, further comprising acetoacetyl-CoA thiolase (AtoB), HMG-CoA synthase (HMGS), HMG-CoA reductase (HMGR), mevalonate kinase (MK), phosphomevalonate kinase (PMK), mevalonate diphosphate decarboxylase (PMD), isopentenyl diphosphate (IPP) isomerase (Idi), and farnesyl diphosphate (FPP) synthase (IspA), which are heterologous to the genetically modified host cell.

13. A method for producing prespatane comprising: (a) providing a genetically modified host cell of claim 1 or a culture thereof, (b) culturing the genetically modified host cell to produce prespatane.

14. The method of claim 13, wherein the culture comprises a biomass or hydrolysate thereof.

15. The method of claim 14, wherein the biomass or hydrolysate thereof, is obtained from poplar.

16. The method of claim 13, further comprising the step of extracting or separating the prespatane from the culture.

17. The method of claim 16, further comprising the step of hydrogenating the prespatane extracted or separated from the culture.

18. The method of claim 16, further comprising the step of introducing a fuel additive to the extracted or separated prespatane.

* * * * *

SEQUENCE LISTING

```
<160> NUMBER OF SEQ ID NOS: 4

<210> SEQ ID NO 1
<211> LENGTH: 341
<212> TYPE: PRT
<213> ORGANISM: Laurencia pacifica

<400> SEQUENCE: 1

Met Ser Leu Ala Asn Asn Ile Ala Pro Thr His Ser Met Arg Ser Asp
1               5                   10                  15

Ser Val Glu Val Gly Phe Asn Lys Leu Arg Phe Thr Ser Phe Thr Ser
            20                  25                  30

Phe Gly Asp Glu Phe Ile Asn Glu His Glu Ala Pro Ala Phe Ile Glu
        35                  40                  45
```

Ser Val Ala Trp Phe Gln Ser Leu Asn Ala Ile Ala Thr Pro Gln His
 50                  55                  60

Leu Lys Ile Val Lys Asn Ala Thr Phe Glu Arg Leu Val Ser Arg Thr
 65                  70                  75                  80

Phe Pro Phe Ala Asp Leu Ala Gly Ala Arg Ile Ala Thr Asp Leu Met
                 85                  90                  95

Ile Leu Thr Phe Leu Ile Asp Asp Leu Ser Asp Val Val Glu Ala Thr
                100                 105                 110

Asp Asp Thr Ala Met His Ala Met Ser Ala Val Glu Gly Gln Val Thr
                115                 120                 125

His Val Leu Arg Gly Gly Thr Pro Arg Pro Gly Glu His Pro Leu Ala
130                 135                 140

Val Ala Met Arg Ser Ile Val Asp Arg Ala Met Leu Thr Tyr Asn Pro
145                 150                 155                 160

Asp Trp Ile Asp Leu Met Arg Lys Glu Phe Ile Thr Tyr Leu Glu Met
                165                 170                 175

Asn Arg Leu Glu Arg Ile Asn Arg Leu Glu Gly Pro Gly Leu Ser Trp
                180                 185                 190

Thr Met Phe Glu Asn Thr Arg Tyr Tyr Ser Ser Cys Val Leu Pro Phe
                195                 200                 205

Leu Tyr Leu Ser Ala Gly Met Gly Cys Thr Gly Cys Pro Ser Thr Val
 210                 215                 220

Leu Ser Val Pro Phe Val Lys Ile Met Thr Asp Leu Thr Val Asn His
225                 230                 235                 240

Val Ala Trp Val Asn Asp Ile Val Gly Ala Asn Lys Glu Arg Lys Glu
                245                 250                 255

Ala Val Asn Asn Asn Ile Val Phe Val Ile Ala Asn Asp Arg Gly Leu
                260                 265                 270

Thr Met Ala Gly Ala Val Lys Asp Ala Val Lys Arg Thr Asn Gln Glu
                275                 280                 285

Cys Glu Val Phe Leu Asn Leu Glu His Arg Leu His Ala Gly Gly Ala
                290                 295                 300

Val Val Asp Gly Asp Asp Leu Phe Asn Tyr Ile Glu Val Leu Lys Tyr
305                 310                 315                 320

Trp Met Arg Gly Ser Leu Asp Trp His Phe Glu Ser Lys Arg Tyr Lys
                325                 330                 335

Val Lys Ala Ser Lys
                340

<210> SEQ ID NO 2
<211> LENGTH: 361
<212> TYPE: PRT
<213> ORGANISM: Streptomyces coelicolor

<400> SEQUENCE: 2

Met His Ala Phe Pro His Gly Thr Thr Ala Thr Pro Thr Ala Ile Ala
  1               5                  10                  15

Val Pro Pro Ser Leu Arg Leu Pro Val Ile Glu Ala Ala Phe Pro Arg
                 20                  25                  30

Gln Leu His Pro Tyr Trp Pro Lys Leu Gln Glu Thr Thr Arg Thr Trp
                 35                  40                  45

Leu Leu Glu Lys Arg Leu Met Pro Ala Asp Lys Val Glu Glu Tyr Ala
 50                  55                  60

Asp Gly Leu Cys Tyr Thr Asp Leu Met Ala Gly Tyr Tyr Leu Gly Ala
 65                  70                  75                  80

```
Pro Asp Glu Val Leu Gln Ala Ile Ala Asp Tyr Ser Ala Trp Phe Phe
                85                  90                  95

Val Trp Asp Asp Arg His Asp Arg Asp Ile Val His Gly Arg Ala Gly
            100                 105                 110

Ala Trp Arg Arg Leu Arg Gly Leu Leu His Thr Ala Leu Asp Ser Pro
        115                 120                 125

Gly Asp His Leu His His Glu Asp Thr Leu Val Ala Gly Phe Ala Asp
    130                 135                 140

Ser Val Arg Arg Leu Tyr Ala Phe Leu Pro Ala Thr Trp Asn Ala Arg
145                 150                 155                 160

Phe Ala Arg His Phe His Thr Val Ile Glu Ala Tyr Arg Glu Phe
                165                 170                 175

His Asn Arg Thr Arg Gly Ile Val Pro Gly Val Glu Glu Tyr Leu Glu
            180                 185                 190

Leu Arg Arg Leu Thr Phe Ala His Trp Ile Trp Thr Asp Leu Leu Glu
        195                 200                 205

Pro Ser Ser Gly Cys Glu Leu Pro Asp Ala Val Arg Lys His Pro Ala
    210                 215                 220

Tyr Arg Arg Ala Ala Leu Leu Ser Gln Glu Phe Ala Ala Trp Tyr Asn
225                 230                 235                 240

Asp Leu Cys Ser Leu Pro Lys Glu Ile Ala Gly Asp Glu Val His Asn
                245                 250                 255

Leu Gly Ile Ser Leu Ile Thr His His Ser Leu Thr Leu Glu Glu Ala
            260                 265                 270

Ile Gly Glu Val Arg Arg Arg Val Glu Glu Cys Ile Thr Glu Phe Leu
        275                 280                 285

Ala Val Glu Arg Asp Ala Leu Arg Phe Ala Asp Glu Leu Ala Asp Gly
    290                 295                 300

Thr Val Arg Gly Lys Glu Leu Ser Gly Ala Val Arg Ala Asn Val Gly
305                 310                 315                 320

Asn Met Arg Asn Trp Phe Ser Ser Val Tyr Trp Phe His His Glu Ser
                325                 330                 335

Gly Arg Tyr Met Val Asp Ser Trp Asp Asp Arg Ser Thr Pro Pro Tyr
            340                 345                 350

Val Asn Asn Glu Ala Ala Gly Glu Lys
        355                 360

<210> SEQ ID NO 3
<211> LENGTH: 5
<212> TYPE: PRT
<213> ORGANISM: Laurencia pacifica
<220> FEATURE:
<221> NAME/KEY: misc_feature
<222> LOCATION: (3)..(4)
<223> OTHER INFORMATION: Xaa can be any naturally occurring amino acid

<400> SEQUENCE: 3

Asp Asp Xaa Xaa Asp
1               5

<210> SEQ ID NO 4
<211> LENGTH: 5
<212> TYPE: PRT
<213> ORGANISM: Laurencia pacifica
<220> FEATURE:
<221> NAME/KEY: misc_feature
<222> LOCATION: (3)..(4)
<223> OTHER INFORMATION: Xaa can be any naturally occurring amino acid
```

```
<400> SEQUENCE: 4

Asp Asp Xaa Xaa Glu
1               5
```